United States Patent
Tabata et al.

(10) Patent No.: US 7,879,017 B1
(45) Date of Patent: Feb. 1, 2011

(54) DISPOSABLE ABSORBENT ARTICLE

(75) Inventors: Kenichi Tabata, Ehime (JP); Hiroshi Ono, Tochigi (JP); Haruhiko Nasa, Tochigi (JP); Kazunori Ito, Ehime (JP); Kazumichi Ogawa, Ehime (JP); Hideki Saiga, Ehime (JP)

(73) Assignees: Daio Paper Corporation, Ehime (JP); Daio Paper Converting Co., Ltd., Ehime (JP); Elleair Paper Rech. Co., Ltd., Tochigi (JP)

( * ) Notice: Subject to any disclaimer, the term of this patent is extended or adjusted under 35 U.S.C. 154(b) by 0 days.

(21) Appl. No.: 10/030,249

(22) PCT Filed: Jul. 14, 2000

(86) PCT No.: PCT/JP00/04755

§ 371 (c)(1),
(2), (4) Date: Jun. 28, 2002

(87) PCT Pub. No.: WO01/05347

PCT Pub. Date: Jan. 25, 2001

(30) Foreign Application Priority Data

| Jul. 14, 1999 | (JP) | 11-200241 |
| Jan. 17, 2000 | (JP) | 2000-007355 |
| Apr. 12, 2000 | (JP) | 2000-110378 |
| Apr. 12, 2000 | (JP) | 2000-110379 |

(51) Int. Cl.
*A61F 13/494* (2006.01)
(52) U.S. Cl. ............... 604/385.23; 604/385.24; 604/385.27; 604/385.28

(58) Field of Classification Search . 604/385.24–385.3, 604/393–396
See application file for complete search history.

(56) References Cited

U.S. PATENT DOCUMENTS

| 4,585,447 A | 4/1986 | Karami |
| 4,695,278 A * | 9/1987 | Lawson ............. 604/385.27 |
| 5,026,364 A * | 6/1991 | Robertson ........... 604/385.3 |

(Continued)

FOREIGN PATENT DOCUMENTS

DE 3741828 C1 * 5/1989

(Continued)

OTHER PUBLICATIONS

Microfilm of the specification and drawings annexed to the request of Japanese Utility Model Application No. 84057/1990 (Laid-open No. 42816/1992) (Oji Paper Co., Ltd. et al.) Apr. 10, 1992.

(Continued)

*Primary Examiner*—Karin M Reichle
(74) *Attorney, Agent, or Firm*—McDermott Will & Emery LLP

(57) ABSTRACT

A disposable absorbent article such as a disposable diaper having standing cuffs around leg portions or a waist portion. The disposable absorbent article has, in a used condition, standing cuffs each having a free portion thereof stand toward the wearer by means of a stretching force of stretching members. Stretching members are respectively provided at the tip end of the free portion and at a portion between the base end and the middle of the free portion and closer to the base end. The standing cuff may not have a plane-gathering cuff at the outer side thereof.

7 Claims, 28 Drawing Sheets

U.S. PATENT DOCUMENTS

| | | | | |
|---|---|---|---|---|
| 5,114,420 A | * | 5/1992 | Igaue et al. | 604/385.26 |
| 5,246,431 A | * | 9/1993 | Minetola et al. | 604/385.28 |
| 5,582,606 A | * | 12/1996 | Bruemmer et al. | 604/385.28 |
| 5,607,416 A | * | 3/1997 | Yamamoto et al. | 604/397 |
| 5,620,431 A | | 4/1997 | LeMahieu et al. | |
| 5,643,243 A | | 7/1997 | Klemp | |
| 5,776,121 A | * | 7/1998 | Roe et al. | 604/385.25 |
| 5,904,675 A | * | 5/1999 | Laux et al. | 604/385.29 |
| 5,911,713 A | | 6/1999 | Yamada et al. | |
| 5,993,433 A | * | 11/1999 | St. Louis et al. | 604/385.27 |
| 6,156,023 A | * | 12/2000 | Yoshioka | 604/385.29 |
| 6,659,993 B2 | * | 12/2003 | Minato et al. | 604/385.27 |

FOREIGN PATENT DOCUMENTS

| | | |
|---|---|---|
| EP | 0 346 477 A1 | 12/1989 |
| EP | 0 648 482 | 10/1994 |
| EP | 0 648 482 | 4/1995 |
| EP | 0 904 759 A2 | 3/1999 |
| GB | 2 233 235 A | 1/1991 |
| JP | 61-239001 | 10/1986 |
| JP | 61-244347 | 10/1986 |
| JP | 62-250201 | 10/1987 |
| JP | 3-111323 | 11/1991 |
| JP | 4-9153 | 1/1992 |
| JP | 4-152947 | 5/1992 |
| JP | 04-161152 | 6/1992 |
| JP | 4-354948 | 12/1992 |
| JP | 05-003891 | 1/1993 |
| JP | 05-028329 | 4/1993 |
| JP | 05-093428 | 12/1993 |
| JP | 06-030963 | 2/1994 |
| JP | 06-021622 | 3/1994 |
| JP | 6-93901 | 11/1994 |
| JP | 7-112003 | 5/1995 |
| JP | 8-10285 | 1/1996 |
| JP | 8-112309 | 5/1996 |
| JP | 8-154971 | 6/1996 |
| JP | 9-24063 A | 1/1997 |
| JP | 09-192169 | 7/1997 |
| JP | 10-113362 | 5/1998 |
| JP | 10-277092 | 10/1998 |
| JP | 10-328234 | 12/1998 |
| JP | 11-104173 | 4/1999 |
| JP | 11-188060 | 7/1999 |
| JP | 11-188062 | 7/1999 |
| JP | 2000-262553 | 9/2000 |
| JP | 2001-025485 | 1/2001 |
| JP | 2001-046431 | 2/2001 |
| JP | 2001-178771 | 7/2001 |
| JP | 2001-293031 | 10/2001 |
| JP | 3429466 | 5/2003 |
| JP | 3677502 | 5/2005 |
| JP | 2005-224619 | 8/2005 |
| JP | 3769545 | 2/2006 |
| JP | 2006-223881 | 8/2006 |
| JP | 2007-000653 | 1/2007 |
| WO | WO 93/09739 A1 | 5/1993 |
| WO | WO 95/07063 | 3/1995 |
| WO | WO 96/31179 | 10/1996 |
| WO | WO 97/15260 | 5/1997 |
| WO | WO 9720532 A1 * | 6/1997 |
| WO | WO 98/08474 | 3/1998 |
| WO | WO 99/20215 | 4/1999 |

OTHER PUBLICATIONS

Notice of Opposition filed by SCA Hygiene Products AB, Issued in corresponding European Patent Application No. 00946345.6-2124, dated on Jun. 21, 2007.

Notice of Opposition filed by The Procter & Gamble Company, issued in corresponding European Patent Application No. 00946345.6-2124, dated on Jun. 15, 2007.

Japanese Office Action issued in Japanese Patent Application No. 2006-086737, dated Jul. 2, 2010.

* cited by examiner

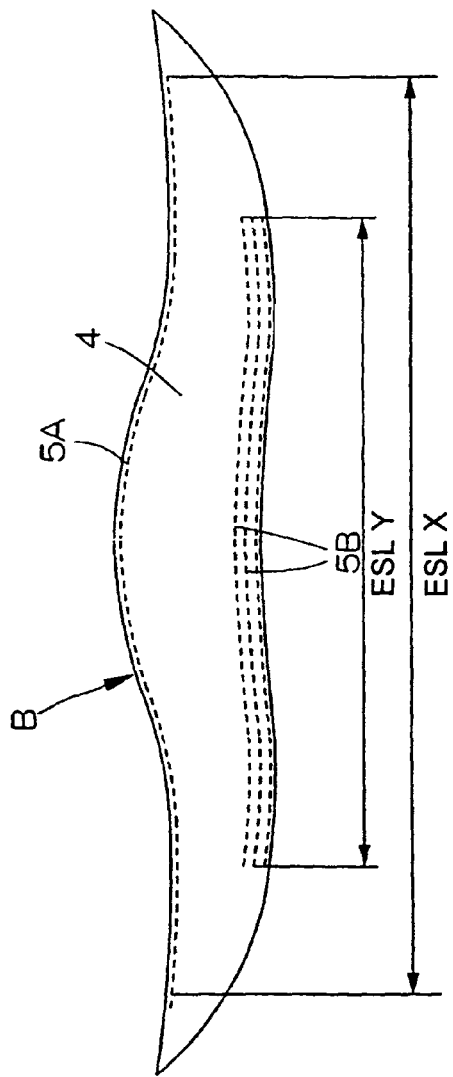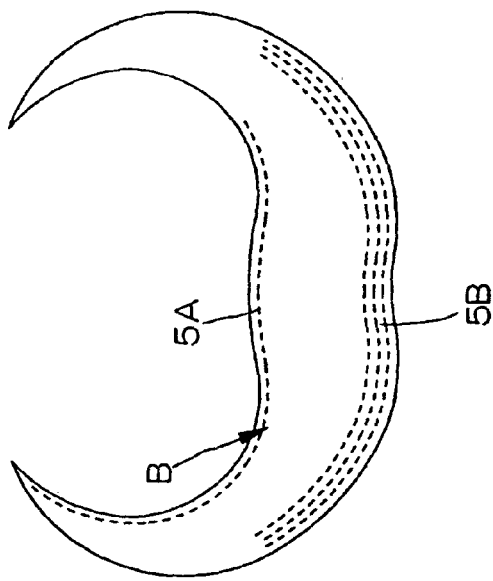
Fig. 9A
Fig. 9B

DISPOSABLE ABSORBENT ARTICLE

FIELD OF THE INVENTION

The invention relates to disposable absorbent articles such as disposable diapers having standing cuffs.

BACKGROUND ART

Various types of disposable diapers have been well known.

One of examples of disposable diapers is disclosed in Japanese Patent Publication No. 94-93901. This publication pertains to a disposable diaper having a dual barrier system which can avoid side leakage using a standing cuff and a gasketing cuff.

However, even though the standing cuff and the gasketing cuff are used in the dual barrier system, the side leakage cannot properly be avoided.

In the conventional disposable article having such dual barrier system, while each gasketing cuff is maintained to encircle a wearer's leg, a distal edge of the corresponding standing cuff is brought into line-contact with a wearer's crotch.

Accordingly, during the use of this article, the location of the distal edge of the standing cuff varies depending on the contacted portion of the wearer's leg by the gasketing cuff. Thus, a line-contacted portion of the wearer's crotch by the distal edge of the standing cuff changes for each application of this article. Such condition means that, this article has incomplete barrier against the side leakage.

The standing cuff of this conventional article should stand slantingly toward the longitudinal centerline of the article. In spite of this, when the article is not used in a proper wearing manner, the standing cuff tends to bend outwardly. In such case, the liquid component of the loose feces may be leaked.

Since the conventional article has the gasketing cuff in addition to the standing cuff, it is natural that the standing cuff should be laterally inboard with respect to the corresponding gasketing cuff. Hence, a distance in the lateral direction of the article formed between the opposite standing cuffs is not enough to obtain a pocket space having a suitable size. (The pocket space with the suitable size is required for capturing surely and holding safely urine and loose feces even when the article is not used in the proper wearing manner and even when the wearer moves to some degree).

In order to facilitate completely the standing cuff, this cuff is required to stand surely with the sufficient height. Then, the standing cuff stands by means of a stretching force of stretching members. In this connection, in the conventional standing cuff, the stretching members extend along the only distal edge thereof. Actually, with only these stretching members, standing ability is not enough.

In order to apply an article such as a diaper, the article is usually put over a wearer's waist and then, moved so as to locate properly. Once the article is applied to the wearer, a friction force is generated due to the contact between the distal edge of the standing cuff and the wearer's skin. Accordingly, even after the article is rearranged so as to locate properly, the distal edge may not be moved together with the article body, but remained at the first position by means of the friction force. This means that the standing cuff cannot stand in proper direction, resulting in unsuitable contact position between the standing cuff and the wearer's skin, during the use of the article.

SUMMARY OF THE INVENTION

Therefore it is a main object of the present invention to provide a disposable absorbent article comprising at least one standing cuff, which can stand surely with the sufficient height at the desirable position, thereby ensuring efficient protection against the leakage of the article.

It is an additional object to provide a disposable absorbent article comprising a pocket space having a suitable size, thereby ensuring capture of urine and loose feces.

It is a further object to provide a disposable absorbent article having a very reliable protection against the side leakage without a gasketing cuff.

It is also an object to provide a disposable absorbent article with ensured protection against the side leakage by conforming both the standing portion and surface-contacting portion of the standing cuff to the movement of a wearer even when the article is used in unsuitable wearing manner. In this article, a boundary between the standing portion and surface-contacting portion is brought into line-contact with the wearer's crotch, then at the same time the surface-contacting portion is brought into surface-contact with the skin at the wearer's leg.

According to the present invention, the disposable absorbent article comprises the standing cuffs, whose free portion stand from a base line toward the wearer by means of the stretching force by the stretching members, during the use of the article. Then, these stretching members extend along the distal edge of the free portion and extend in the base line-side with respect to the longitudinal centerline of the free portion.

In such configuration, the standing cuff can stand by means of the contracting force by the stretching members, which extend in the base line-side with respect to the longitudinal centerline of the free portion. Further, the standing cuff can stand also by means of the contracting force by the stretching members, which extend along the distal edge of the free portion. Accordingly, the base portion of the standing cuff, first, stand by means of the contracting force by the stretching members, which extend in the base line-side with respect to the longitudinal centerline of the free portion. In addition, the contracting force by the stretching members, which extends along the distal edge of the free portion, is applied to the standing cuff. As a result, the standing cuff can stand surely with the sufficient height.

As stated above, when an article such as a diaper is applied to a wearer, the article is usually put over a wearer's waist and then, rearranged so as to locate properly. During this application, a friction force is generated due to contact between the distal edge of its standing cuff and wearer's skin. In the conventional article, after the article is rearranged, the distal edge may remain at the first position by means of the friction force. Accordingly, the standing cuff cannot stand in proper direction. On the contrary, according to the present article, such situation is not caused. Precisely, when the article is rearranged, the distal edge is moved together with the article body so that the standing cuff can stand at a desired position.

Therefore, in the article of the present invention, the standing cuff can stand surely with the sufficient height at the desired position, which results in efficient protection against the leakage of the diaper.

Under this spirit of the present invention, several embodiments having the above advantages are proposed. Now, these embodiments will be divided into some groups in order to give close explanation.

[The First Group: An Article, where Each Standing Cuff Comprises a Surface-Contacting Portion and a Standing Portion]

In the basic aspect of the first group, a disposable absorbent article comprises standing cuffs for wearer's legs, each of which has a free portion. The free portion stands toward a wearer from a base line by means of the stretching force of stretching members, during the use of the article. Such article has the following characteristics. Precisely, the free portion, in the stretched state, comprises a standing portion, which stands slantingly toward the longitudinal centerline of the article, and a surface-contacting portion, which outwardly folds back halfway upon itself. In addition, the stretching members extend on the above surface-contacting portion and on the standing portion, respectively.

By means of the standing cuff for the wearer's leg, even if the wearer moves to some degree after the application of the article, both the standing portion and the surface-contacting portion conform to the movement of the wearer. Accordingly, a boundary between the standing portion and surface-contacting portion may be surely brought into line-contact or thin belt-contact with a wearer's crotch. At the same time, the surface-contacting portion is brought into surface-contact with the wearer's leg. Thus, reliable protection against the side-leakage can be obtained. Therefore, even if the article is used in the unsuitable manner, the side-leakage can be prevented completely.

In the front end and back end of the article in its longitudinal direction, the above standing portion lies laterally toward the longitudinal centerline of the article so as to be fixed to the article body, while the above surface-contacting portion folds back halfway upon the standing portion. By doing so, in the leg portion of the article, which is to encircle the wearer's leg, the proper standing of the standing portion can be surely obtained as shown in FIG. 2B.

It is preferable that plural stretching members extend on the above surface-contacting portion, at certain intervals in the lateral direction. Then, also on the above standing portion, a plurality of stretching members may extend, at certain intervals in the lateral direction. By providing a plurality of stretching members in the above surface-contacting portion and the standing portion, at certain intervals in the lateral direction, respectively, the standing effect and surface-contact effect can be improved.

When a plurality of stretching members extend on the above surface-contacting portion and extend on the standing portion, at certain intervals in the lateral direction, respectively, the relation between the stretching members of the surface-contacting portion and those of the standing portion will be stated. The stretching member extending in the surface-contacting portion may be small in diameter and large in contractility. On the other hand, the stretching member extending in the standing portion is large in diameter and small in contractility. By doing so, the surface-contacting portion may be brought into contact softly with the wearer's leg, further, high protection against the side-leakage can be ensured, while the standing portion can stand surely with the large standing force. In addition, the following advantages can be found. Precisely, the standing cuffs are able to bend halfway back upon themselves very smoothly in the operation process for the production of the articles. Further, such folding of the standing cuffs may be maintained very well, during the both storage and use of the articles.

As one example of this embodiment, a disposable absorbent article having the following characteristics is provided. The article comprises standing cuffs for wearer's legs. Each standing cuff comprises a free portion, which laterally extends inboard with respect to a base line defined by the boundary. Then, the free portion stands toward the wearer from the base line by means of stretching the force by the stretching members, during the use of the article. In the article, an absorbent structure is disposed between a liquid pervious sheet on its wearer-side and a liquid impervious sheet on its back-side. Then, a back sheet is disposed at the back-side of the liquid impervious sheet so as to cover the liquid impervious sheet. The above liquid pervious sheet and liquid impervious sheet laterally extend beyond the side edges of the absorbent structure to thereby form extended peripheral side portions. The standing cuff is formed with a standing sheet, which is substantially liquid impervious. This standing sheet and the above back sheet laterally extend beyond the side edges of the above liquid pervious sheet and liquid impervious sheet to thereby form extended peripheral side portions. The base line of the above standing cuff is disposed in the peripheral side portion of the above liquid impervious sheet. The above free portion of the standing cuff comprises a standing portion and a surface-contacting portion, both of which extend longitudinally. The standing portion stands slantingly from the base line toward the longitudinal centerline of the article. On the other hand, the surface-contacting portion folds back halfway. Then, the stretching members extend on the standing portion and surface-contacting portion, respectively.

In this embodiment, leakage from the article to the back-side may be constrained by the liquid impervious sheet. Accordingly, the back sheet may be formed with e.g. a hydrophobic non-woven fabric, which causes soft feeling of the article for the wearer. The liquid pervious sheet and liquid impervious sheet laterally extend beyond the side edges of the absorbent structure to thereby form extended peripheral side portions. The substantially liquid impervious standing sheet, with which the standing cuff is formed, and the above back sheet laterally extend beyond the side edges of the above liquid pervious sheet and liquid impervious sheet to thereby form extended peripheral side portions. The base line of the above standing cuff is disposed on the above peripheral side portion of the liquid impervious sheet. Accordingly, the side-leakage can be surely constrained.

It is possible to provide plane-gathering cuffs outboard with respect to the above standing cuffs. However, it is preferable that the plane-gathering cuff is not provided. By omitting the plane-gathering cuff, even if the article is not applied in proper manner, urine and loose fecal material can be surely captured by a wide pocket space formed between the standing cuffs.

[The Second Group: An Article where the Effective Stretching Length of Stretching Member for Standing is Shorter than that of Stretching Members for Contacting]

In the basic aspect of the second group, a disposable absorbent article comprises standing cuffs for wearer's legs, each of which has a free portion. The free portion stands toward the wearer from a base line by means of a stretching force of stretching members, during the use of the article. Such article has the following characteristics. Precisely, the lateral length of the above free portion is equal to or longer than 10 mm. Then, the stretching members for contacting extend along the distal edge of the above free portion, while the stretching members for standing extend in the base line-side with respect to the longitudinal centerline of the free portion. Further, the effective stretching length of the above stretching member for standing is shorter than that of stretching members for contacting.

The stretching stress of the above stretching members for standing may be larger than that of the above stretching members for contacting.

When the elongation of the portion provided with the above stretching member for contacting is 60% to 150%, its stretching stress can be 0.10 N to 1.30 N (per the width of 15 mm and the length of 100 mm). Then, when the elongation of the portion provided with the stretching member for standing is 60% to 150%, its stretching stress can be 0.20 N to 2.00 N (per the width of 15 mm and the length of 100 mm). The above stretching stress of the latter portion is larger than that of the former portion.

The operation and effect of the above configuration will be stated below.

The standing cuff may comprise a double sheet formed by folding back the standing sheet, wherein the base portion of the double sheet folded back at its distal edge is fixed to the wearer's side surface of the article; the boundary between the base portion and the unfixed free portion defines the base line from which the standing cuff stands; and the above-said stretching members for standing and stretching members for contacting are included and fixed within the double standing sheet in the stretched state.

The standing cuff may also comprise a double standing sheet formed by folding back the standing sheet which comprises two overlapped sheets of the same or a different kind, wherein the base portion of which is fixed to the wearer's side surface of the article; the boundary between the base portion and the unfixed free portion defines the base line from which the standing cuff stands; and the above-said stretching members for standing and stretching members for contacting are included and fixed within the double standing sheet in the stretched state.

Since the standing cuff comprises the double standing sheet the protection against the leakage can be improved, in addition, the shape of the standing cuff can be maintained very well, thus, the standing cuff can be efficiently prevented from curling, during the use of the article.

A water proof sheet may be disposed within the double standing sheet.

As stated above, the disposable absorbent article comprises the standing cuffs for the wearer's legs, each of which has the free portion. The free portion stands toward the wearer from the base line, from which the standing cuff stands by means of the stretching force by the stretching members, during the use of the article. The lateral length of the above free portion is equal to or longer than 10 mm. The stretching members for contacting extend along the distal edge of the above free portion, while the stretching members for standing extend in the base line-side with respect to the longitudinal centerline of the free portion. The above free portion longitudinally extends to form front end-side portion and back end-side portion, which are fixed to the wearer's side surface of the article body. At least in the front end-side of the article, the fixed front end-side portion initiates from an upper line in the distal edge side of the free portion and from a lower line in the proximal edge-side of the free portion. Then, the upper line locates closer to the front end of the article than the lower line. As a result, the effective stretching length of the above stretching member for standing is shorter than that of stretching members for contacting.

[The Third Group: An Article where Stretching Members for Lifting are Fixed Along the Opposite Sides of Absorbent Structure and Laterally Inboard with Respect to Base Lines for Standing Cuffs]

In the basic aspect of the third group, a disposable absorbent article comprises an absorbent structure, which absorbs liquid coming down through a liquid pervious top sheet and which includes an absorbent core having stiffness to some degree. In addition, the article comprises standing cuffs on or adjacent to the above absorbent structure at its both sides. Each standing cuff has a free portion, which stands toward the wearer from the base line by means of the stretching force of stretching members, during the use of the article. Such article has the following characteristics. Precisely, the above stretching members extend along the distal edge of the above free portion and extend in the base line-side with respect to the longitudinal centerline of the free portion. Further, stretching members for lifting are longitudinally fixed along the opposite sides of the absorbent structure and laterally inboard with respect to the base lines for the standing cuffs, in the stretched state.

For the complete protection against the side-leakage of body exudates, it is important that the standing cuff stand with the sufficient height. In order to attain this, the standing cuff may have a large width for the sufficient standing height and be fixed to the article at the front and end thereof. However, in this case, at the front end-side portion and back end-side portion in the longitudinal direction of the article, the distal edge of the standing cuff is laterally inboard. Accordingly, since the standing of the free portion is influenced by such configuration, even the free portion has the large width, it does not stand with sufficient height but just lies with sufficient length. That is to say, the standing cuffs cannot stand with the sufficient height toward the wearer's skin.

In order to solve this problem, the stretching members for lifting are longitudinally fixed along the opposite sides of the absorbent structure and laterally inboard with respect to the base lines for the standing cuffs, in the stretched state. By doing so, the absorbent structure is deformed so as to stand toward the wearer. In addition to this standing of the absorbent structure, the standing cuffs stand from the base lines, which are disposed laterally outboard with respect to the stretching members for lifting. This means that the article can stand with large height, resulting in a deep pocket space and improved fitting with the wearer's skin. As a result, by utilizing only standing cuffs, the side-leakage can be surely constrained.

In an alternative aspect of the third group, a disposable absorbent article comprises an absorbent structure, which absorbs liquid coming down through a liquid pervious top sheet and which includes an absorbent core having stiffness to some degree. Further, this absorbent structure is configured so as to protect against the leakage of the liquid, which is to be absorbed into a liquid impervious back sheet covered on the under surface of the above absorbent structure. In addition, the absorbent structure is disposed on the wearer's side surface of a flexible overall sheet. The absorbent article further comprises standing cuffs, which have free portions, respectively. The standing cuffs are disposed on the opposite sides of the above absorbent structure or opposite outboard adjacent sides to the above absorbent structure. Each free portion stands toward the wearer from the base line, from which the standing cuff stands by means of the stretching force by the stretching members, during the use of the article. Such article has the following characteristics. Precisely, the above stretching members extend along the distal edge of the above free portion and extend in the base line-side with respect to the centerline of the free portion. Further, stretching members for lifting are longitudinally fixed along the opposite sides of the absorbent structure and laterally inboard with respect to the base lines for the standing cuffs, in the stretched state.

In this aspect, in order to produce this article, the absorbent structure is disposed on the wearer's side surface of the overall sheet. Then, since the overall sheet is flexible, the absorbent structure can stand toward the wearer's skin.

Each side portion of the above liquid impervious back sheet comprises a double portion formed by folding the side edge of the back sheet back upon itself so as to cover the over surface of the side portion of the absorbent structure. The above stretching member for lifting may be disposed between the above liquid impervious back sheet and the above absorbent structure.

Due to the configuration where the liquid impervious back sheet is folded so as to cover the over surface of the opposite side portions of the absorbent structure, side leakage of the exudates, which has been absorbed into the absorbent structure, does not occur. In addition, since the above stretching members for lifting are disposed between the above liquid impervious back sheet and the above absorbent structure, the absorbent structure can stand surely by means of the stretching members for lifting.

The above absorbent structure comprises the above absorbent core and crepe paper. The opposite sides of the absorbent core, in their longitudinally middle portions, are cut away so as to contour the leg portions of the article. The crepe paper has the shape of rectangle and totally covers the over and under surfaces of the absorbent core. The above stretching members for lifting, in their longitudinally middle portions corresponding to the portions, extend so as not to be superposed on the cut away portions of the absorbent core, respectively. Then, the above stretching members for lifting, in the front end portion and back end portion thereof, extend so as to be superposed on the laterally extended opposite portions of the absorbent core, respectively.

In order to attain fitting of the article around the wearer's legs, the opposite sides of the absorbent core, in their longitudinally middle portions corresponding to the leg portions, are cut away so as to contour the leg portions of the article. That is to say, it is preferable that the absorbent structure comprises the absorbent core, whose opposite sides are cut away as state above, and the crepe paper, which has the shape of rectangle and totally covers the over and under surfaces of the absorbent core. Here, the absorbent structure comprises the crepe paper having the absorbency for the exudates. It is possible that an absorbent core has the shape of rectangle and the whole length of the stretching members for lifting extends so as to be superposed on the absorbent core. In this case, large stretching stress is required to deform the whole length of the absorbent core for its standing, because it has stiffness to some degree. In order to solve this problem, as stated above, the location of the stretching members for lifting is designed. Precisely, these members, in the leg portions, extend so as not to be superposed on the cut away portions of the absorbent core, and in the front end portion and back end portion, extend so as to be superposed on the laterally extended opposite portions of the absorbent core. By doing so, each stretching member for lifting is not required to have large stretching stress. Further, the crepe paper is able to surely stand at its portions corresponding to the cut away portions of the absorbent core. It should be noted that the laterally extended opposite portions of the absorbent core are necessary for ensuring enough absorbency of the article.

[The Fourth Group: An Article Having One or Two Standing Cuff(s) for Wearer's Waist]

In the basic aspect of the fourth group, a disposable absorbent article comprises a standing cuff for wearer's waist having free portions. Each free portion stands toward the wearer from the base line by means of the stretching force of stretching members, during the use of the article. Such article has the following characteristics. Precisely, the above stretching members laterally extend along the distal edge of the above free portion and laterally extend in the base line-side with respect to the laterally extending centerline of the free portion.

In another aspect of the fourth group, a disposable absorbent article can comprise laterally extending a standing cuff for wearer's waist having free portions and each free portion stands toward the wearer from the base line by means of the stretching force of stretching members, during the use of the article. Then, such article particularly has the following characteristics. Precisely, stretching members for contacting laterally extend along the distal edge of the above free portion and stretching members for standing laterally extend in the base line-side with respect to the laterally extending centerline of the free portion. In addition, means for gathering the article is not provided at the waist flap of the article.

The standing cuff for the wearer's waist laterally extends for the length of at least 10 mm.

It is preferable that the stretching stress of the stretching members for standing is larger than that of the stretching members for contacting.

Concretely, when the elongation of the portion provided with the above stretching member for contacting is 20% to 90%, its stretching stress can be 0.05 N to 1.00 N (per the width of 15 mm and the length of 100 mm). Then, when the elongation of the portion provided with the stretching member for standing is 20% to 90%, its stretching stress can be 0.10 N to 1.50 N (per the width of 15 mm and the length of 100 mm). The stretching stress of the latter can be larger than that of the former. The above stretching stress of the latter portion is larger than that of the former portion.

Fixed portions are located at the opposite sides of the standing cuff for the wearer's waist. The side edge of each fixed portion is inboard with respect to the side edge of the article with the distance of 1 mm to 40 mm.

The standing cuff for the wearer's waist comprises a double standing sheet folded back at the free edge, the base portion of the double standing sheet is fixed to the wearer's side surface of the article, the boundary between the fixed portion and the unfixed free portion defines the base line of the standing cuff for the wearer's waist, and the above-said stretching members for contacting and stretching members for standing are included and fixed within the double standing sheet in the stretched state.

The standing cuff may comprise a double standing sheet formed by folding back the standing sheet which comprises two overlapped sheets of the same or a different kind, wherein the base portion of which is fixed to the wearer's side surface of the article; the boundary between the base portion and the unfixed free portion defines the base line of the standing cuff for the wearer's waist and the above-said stretching members for standing and stretching members for contacting are included and fixed within the double standing sheet in the stretched state.

A water proof sheet can be disposed within the double standing sheet.

The significance of the above aspects including the standing cuff for the wearer's waist will be stated below.

BRIEF DESCRIPTION OF THE DRAWINGS

FIGS. 9A and 9B are views for illustrating the standing states of its standing cuff.

BEST MODE FOR CARRYING OUT THE INVENTION

Now, the present invention is described more closely, referring to the following embodiments taken in conjunction with the accompanying drawings. The disposable absorbent articles in accordance with the present invention can be applied to not only disposable diapers but also sanitary napkins and the like. As the disposable diapers, there are pant-type disposable diapers and disposable diapers with fastening tapes.

The First Embodiment

Figure 1:
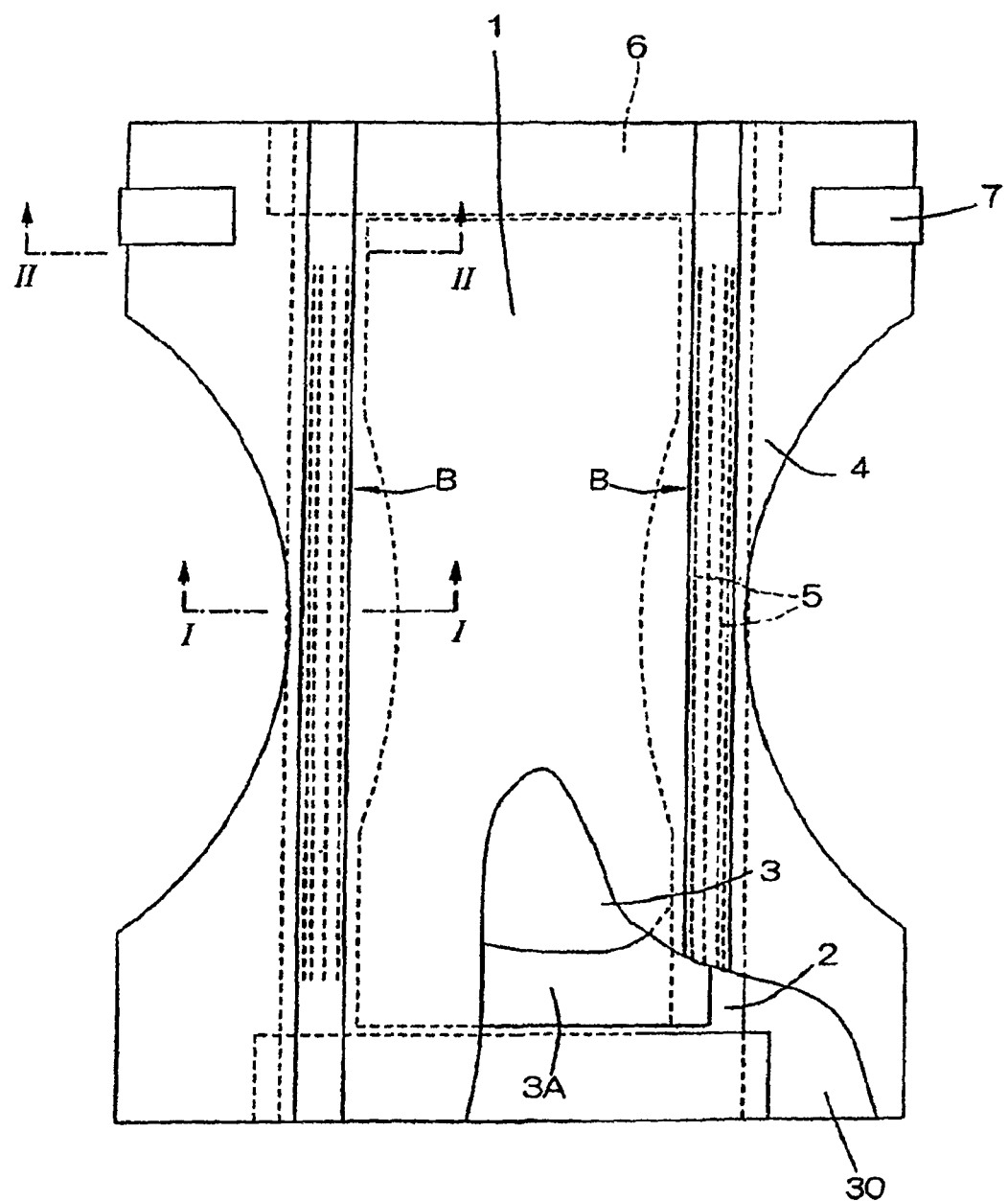
FIG. 1 is a plan view of a disposable diaper embodiment of the present invention having portions cut away, when the diaper is in its stretched state.
Figure 2A:
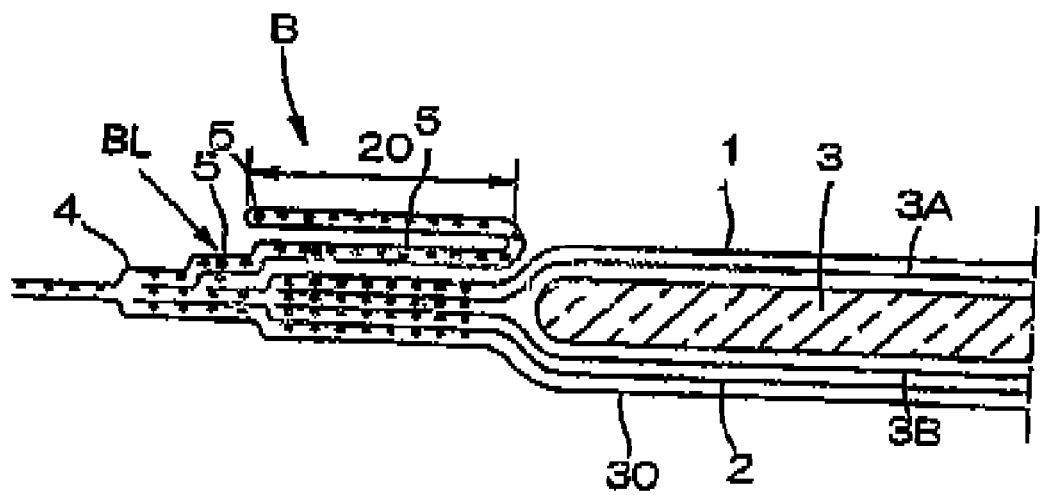
FIGS. 2A and 2B are sectional views taken on line I-I of FIG. 1 when the diaper is in its stretched state and wearing state, respectively.
Figure 2B:
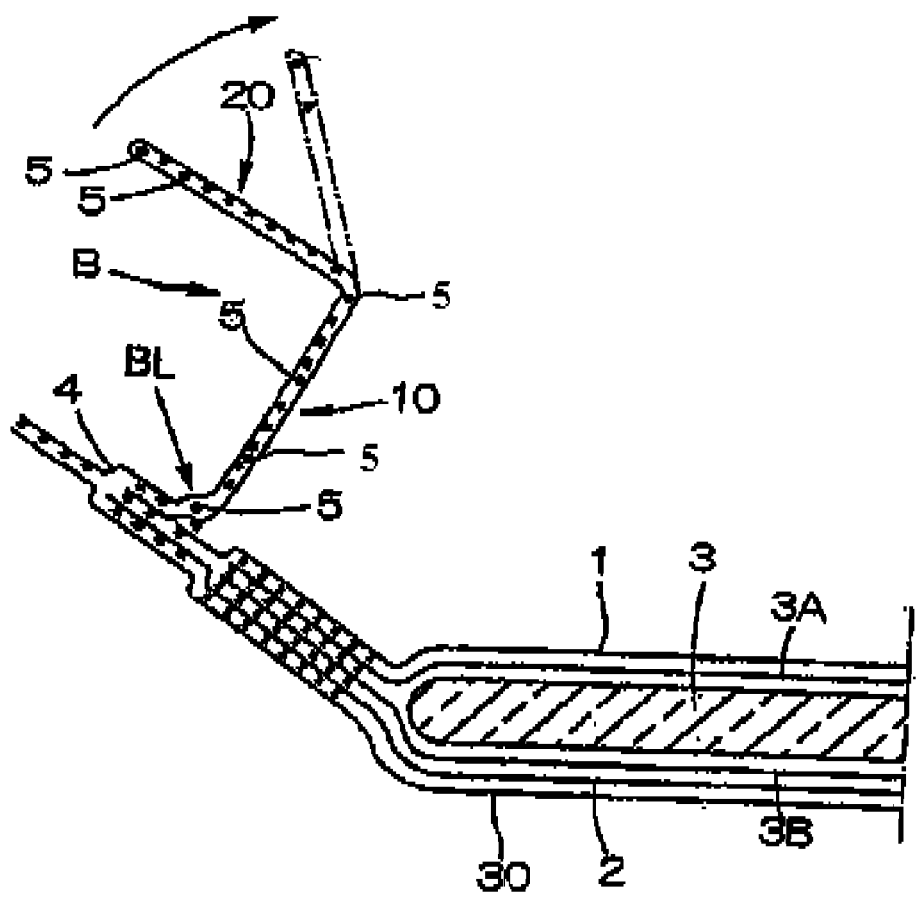
Figure 3:
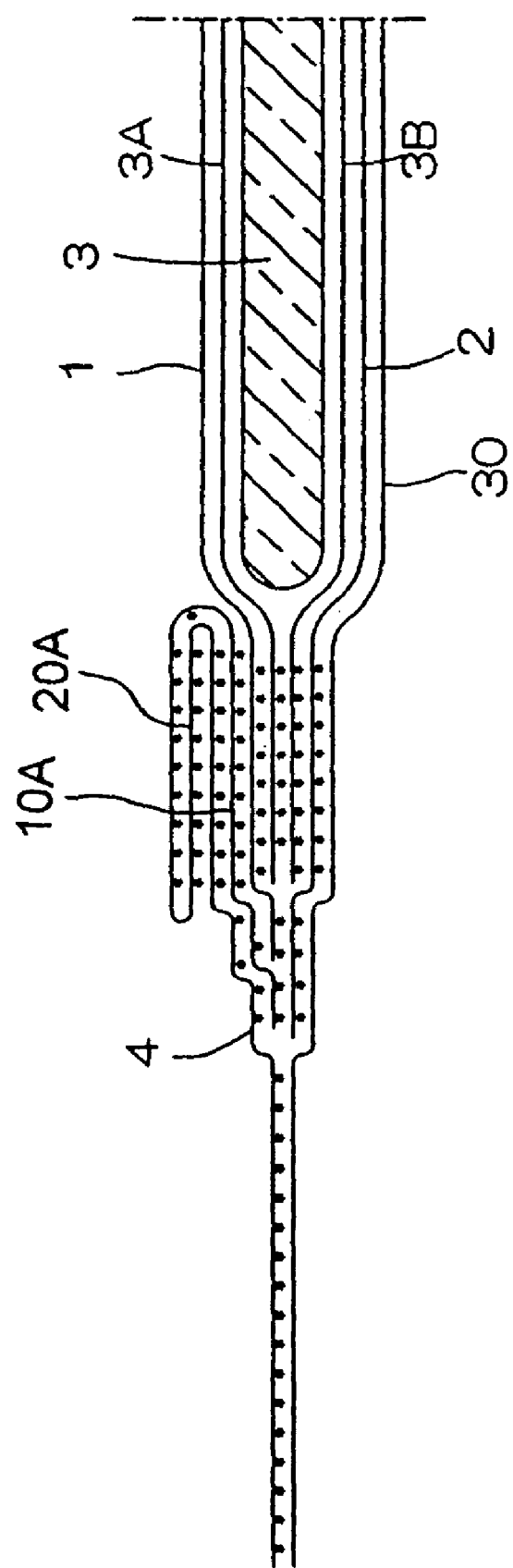
FIG. 3 is a sectional view taken on line II-II of FIG. 1.

FIGS. 1 to 3

A disposable diaper shown in FIGS. 1 to 3 comprises a liquid pervious sheet 1, which is manufactured from e.g. non-woven fabric, a liquid impervious sheet 2, which is manufactured from e.g. polyethylene, and an absorbent core 3 disposed between these sheets 1 and 2. This absorbent core 3 is manufactured from e.g. flocculent pulp and has the shape of rectangle or preferably hourglass as shown in FIG. 1, and stiffness to some degree. This absorbent core 3 is coated with a top tissue paper 3A and a back tissue paper 3B as absorbing sheets to thereby form an absorbent structure. As shown in FIGS. 2A and 2B, the top and back tissue papers 3A and 3B, as the absorbent sheets, laterally extend beyond the side edges of the absorbent core 3 to thereby form extended peripheral side portions in the opposite leg portions of the diaper. These tissue papers 3A and 3B have absorbency of urine also in their extended peripheral side portion.

The liquid impervious sheet 2 has the shape of rectangle with the width being larger than that of the absorbent structure. Then, a back sheet 30, which has the shape of hourglass and which is manufactured from e.g. non-woven fabric, is provided so as to cover externally the liquid impervious sheet 2. The side edge of the back sheet 30 and the side edge of the liquid pervious sheet 1 are conformed to the shape of the diaper as an article.

The liquid pervious sheet 1 has the shape of rectangle with the width being larger than that of the absorbent structure so as to laterally extend beyond the side edges of the absorbent structure with a short distance, and is fixed to the liquid impervious sheet 2 by e.g. hot melt adhesive. (In the diaper of the present embodiment, fixed portions including this extended peripheral side portion of the liquid pervious sheet 1 are represented by symbols *.)

Standing cuffs B are formed at the opposite sides of the disposable diaper so as to stand around the wearer's legs by projecting toward the wearer. The standing cuff B is formed with a standing sheet 4, which is continuous in the substantially lateral direction, and one or a plurality of stretching members of rubber strands as shown in the Figures. The reference numeral 6 designates a stretching member for constraining leakage of the diaper from its front and back end. The reference numeral 7 designates a tape-tab as attachment means.

Further, the standing cuff B is made double by folding the inside of the standing sheet 4 inwardly so as to be shorter than the outside. The stretching members 5 for the wearer's leg are included and fixed within the standing cuff B with e.g. hot melt adhesive.

The internal side of the double standing sheet initiates at a proximal edge fixed to the side edge of the liquid pervious sheet 1, and is fixed to the liquid impervious sheet 2 along its extended peripheral side portion with e.g. hot melt adhesive in the laterally outboard portion with respect to the proximal edge. The undersurface of the external side of the double standing sheet is fixed to the back sheet 30 with e.g. hot melt adhesive.

As stated above, the proximal edge where the internal side of the double standing sheet is fixed to the liquid pervious sheet 1, defines the base line BL from which each standing cuff B stands. In the leg portion of the diaper, the laterally inboard portion with respect to this base line BL is not fixed to the diaper body but free therefrom. Further, this inboard portion folds back halfway so as to be divided functionally and conceptually into two portions, a standing portion 10 which stands toward the longitudinal centerline of the diaper and a surface-contacting portion 20 which bends outwardly.

The back sheet 30 is fixed to the external side of the double standing sheet and to the liquid impervious sheet 2 with e.g. hot melt adhesive.

As shown in FIG. 3, in the front and back ends of the standing cuff B in its longitudinal direction, the portion corresponding to the above-said standing portion 10A (the extension of the standing portion 10) is fixed to the diaper body, concretely to the external surface of the liquid pervious sheet 1, by laying the portion 10A toward the longitudinal centerline of the diaper, while the portion corresponding to the above-said surface-contacting portion 20A (the extension of the surface-contacting portion 20) being folded back and inverted, is fixed to the portion corresponding to the standing portion 10A.

In a basic aspect, at least one stretching member 5 extends on the surface-contacting portion 20. Preferably, the stretching member 5 extends along the side edge of the surface-contacting portion 20. Further, it is preferable that the stretching member 5 extends also on the standing portion 10.

In the more preferable aspect, the stretching members 5, 5 . . . extend in the vicinity of the base line BL for the standing portion 10, in the vicinity of the distal edge of the double standing sheet, and in the vicinity of the side edge of the surface-contacting portion 20. In addition, a plurality of stretching members 5, 5 . . . preferably extend in the vicinity of the side edge of the surface-contacting portion 20 as shown. Additionally, in order to improve the standing ability of the standing portion 10, a plurality of stretching members 5, 5 . . . may further extend on the standing portion 10. In FIGS. 2A and 2B are shown six stretching members in total.

In FIGS. 2A and 3, the diaper is in its longitudinally stretched state. Actually, when the diaper is applied to the wearer, it defines a boat-form, while the contracting force is applied to it by means of the stretching members 5, 5 . . . . Therefore, during the use of the diaper, in its leg portion, the standing cuff B stands as shown in FIG. 2B by means of the above contracting force, but in its front end and back end, it keeps the state shown in FIG. 3.

In this case, the extended peripheral side portion of the upper and lower tissue papers 3A and 3B is deformed and lifted. At the same time, the absorbent core 3 is slightly deformed and lifted. Thus, a deep pocket space is formed in the diaper.

In addition, in such lifted state, the contracting force by the stretching members 5, 5 . . . is applied to the standing cuff B itself. Therefore, the standing portion 10 is able to stand in the substantially vertical direction. The surface-contacting portion 20 also stands vertically (see the surface-contacting portion 20 shown by the phantom line in FIG. 2B). However, since the portion corresponding to the surface-contacting portion (the extension of the surface-contacting portion 20) being folded back and inverted is fixed to the portion corresponding to the standing portion 10A, vertical standing is limited and the surface-contacting portion 20 stands facing outward and keeping the standing force in the vertical direction (shown with an arrow in FIG. 2B).

As a result, the surface-contacting portion 20 always fits flat around the wearer's leg.

The space formed between the standing portions 10, 10 forms a pocket space for enclosing urine and loose feces. When they are captured in the pocket space, the urine is absorbed into the absorbent core 3 through the liquid pervious sheet 1, and the solid component of the loose feces is prevented from flowing beyond the standing cuff B due to its standing portion 10. If the urine and the liquid component of the loose feces should flow beyond the distal edge of the standing portion 10, the surface-contacting portion 20 functions as a stopper against the side-leakage.

In the above embodiment, it is preferable that the standing sheet, which forms the standing cuff, is not liquid pervious but liquid impervious. Alternatively, it is also preferable that the standing sheet is treated with e.g. silicone so as to have water repellency. In the above embodiment, the base line BL for the standing sheet for the wearer's leg is on the liquid pervious sheet 1 and in the laterally outboard portion the standing sheet 4 is fixed to the back sheet 30. However, in alternative embodiment, the back sheet 30 is not used, instead, the liquid impervious sheet 2 extends to the side edge of the diaper and the standing sheet 4 may be fixed to the liquid impervious sheet 2.

The relation between the stretching member 5 of the surface-contacting portion 20 and the stretching member 5 of the standing portion 10 will be stated. It is preferable that the stretching member 5 of the surface-contacting portion 20 is small in diameter and large in contractility, while the stretching member 5 of the standing portion 10 is large in diameter and small in contractility. Concretely, when the strand of rubber is used as the stretching member, the stretching member 5 of the surface-contacting portion 20 has the size of 400 d to 640 d and the contraction percentage of 160% to 300%. On the other hand, the stretching member 5 of the standing portion 10 has the size of 640 d to 2100 d and the contraction percentage of 150% to 250%.

The Second Embodiment

FIG. 4

Figure 4:
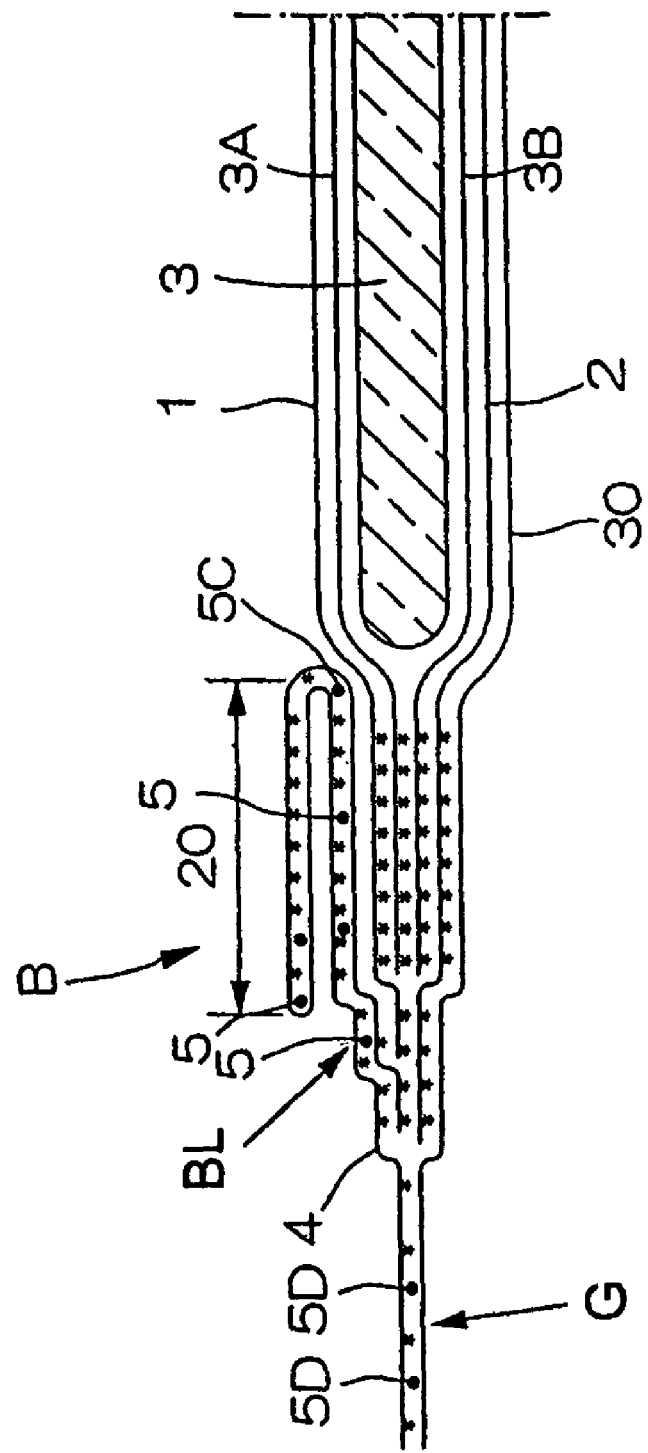
FIG. 4 is a view similar to FIG. 2 showing the disposable diaper second embodiment.

FIG. 4 depicts the second embodiment. The second embodiment differs from the first embodiment in that the diaper of the second embodiment is provided with a plane-gathering cuff G which is gathered by means of the contracting force by stretching members 5D, 5D . . . and brought into surface-contact with the wearer's skin. Such provision of the stretching member 5C gives an advantage of reliable surface-contact of a surface-contacting portion 20.

The Third Embodiment

FIGS. 5 to 11

When the quantity of body exudate is large, particularly a diaper used for an adult, the diaper is required to have higher absorbency from the viewpoints of absorbency and economy. In this situation, the diaper has, over an absorbent core, further an absorbent pad or pad type diaper as complementary means. If the diaper has the absorbent pad, there is no standing cuff. On the other hand, if the diaper has the pad type diaper, the pad type diaper has standing cuffs at the opposite sides thereof. The absorbent pad and pad type diaper, which are superposed on the wearer's side surface of the diaper body, are called "complementary pads".

However, when the complementary pad is superposed on the wearer's side surface of the diaper body, there may be problems as follows. The thickness of the resultant diaper is increased due to the superposed complementary pad. Further, in the resultant diaper, since the absorbent core of the complementary pad is added to the absorbent core of the original diaper body, the stiffness of the resultant diaper is too strong. This causes the difficulty in the deforming of the standing cuffs. Accordingly, no matter how much increased the distance between the standing cuffs, it is difficult to obtain the close contact formed between the standing cuffs and the wearer's skin. This means that the standing cuffs do not serve sufficiently.

In order to solve this problem, it is noticed that the gathering force by the standing cuff is increased for keeping tightness of the surface-contact between the standing cuff and the wearer's skin. However, too large gathering force causes strong pressure to the wearer, resulting in severe discomfort for the wearer.

Therefore, the third embodiment shown in FIGS. 5 to 11 is proposed.

Figure 5:
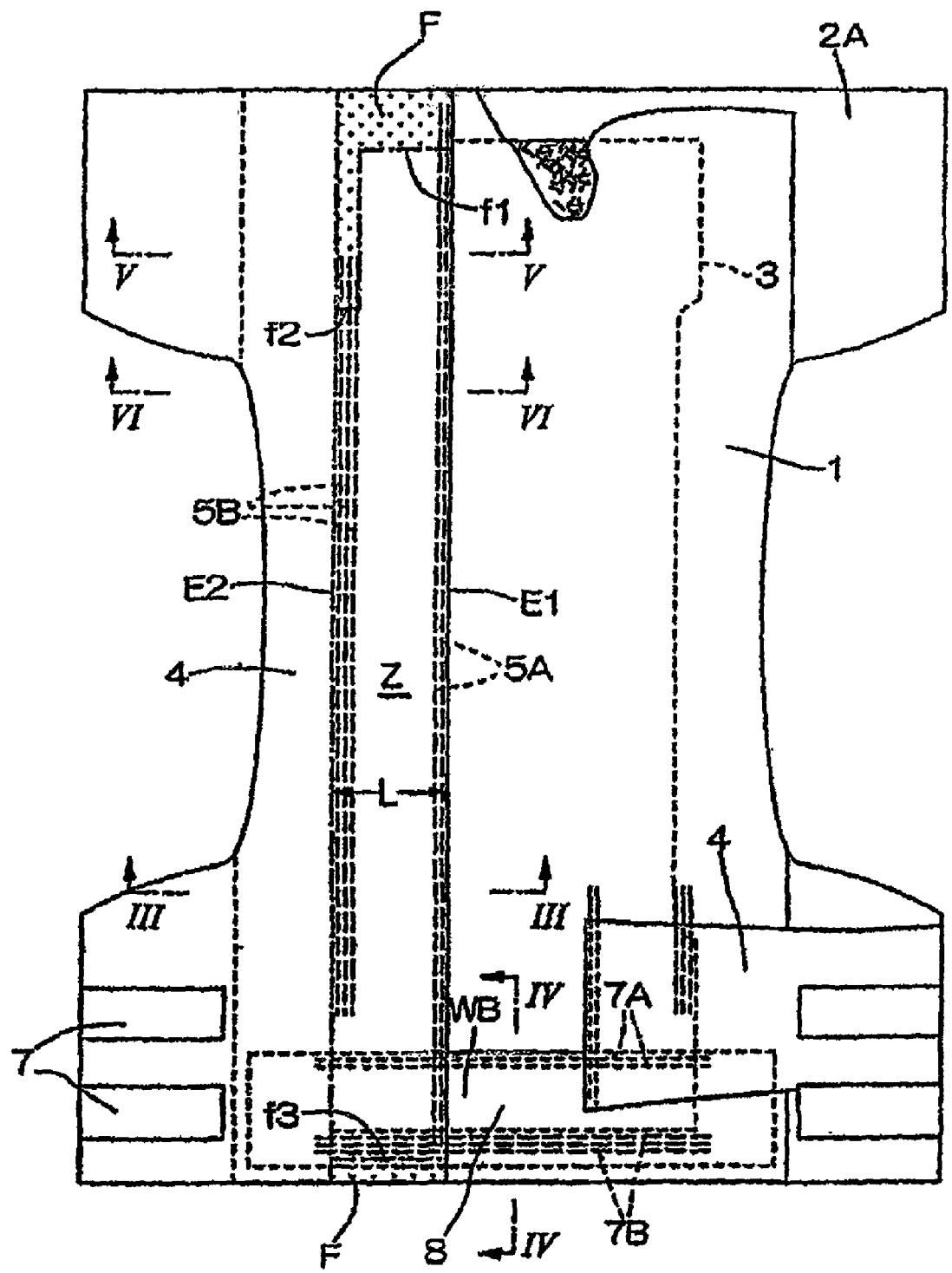
FIG. 5 is a plan view of the disposable diaper alternative embodiment having portions cut away, when the diaper is in its stretched state.

A disposable diaper depicted in FIG. 5 is a diaper with tape-tab fastening means. This diaper comprises a liquid pervious top sheet 1, a liquid impervious back sheet 2A and an absorbent core 3 disposed between these sheets 1 and 2A. The liquid pervious top sheet 1 is manufactured from e.g. nonwoven fabric or porous film and has the shape of e.g. rectangle. Then, the liquid impervious back sheet 2A is manufactured from e.g. polyethylene, poly-laminated non-woven fabric or material with micro voids being pervious to vapors and impervious to liquid, and has the shape of hourglass. The absorbent core 3 is manufactured from e.g. flocculent pulp and has the suitable shape such as rectangle or hourglass, and stiffness to some degree. Highly absorptive polymer may be added into the absorbent core 3. This absorbent core 3 may be coated with a top tissue paper 3A and a back tissue paper 3B as absorbing sheets to thereby form an absorbent structure.

The liquid pervious top sheet 1 has the shape of rectangle with the width being larger than that of the absorbent structure so as to laterally extend beyond the side edges of the absorbent structure with a short distance and is fixed to the liquid impervious back sheet 2A by e.g. hot melt adhesive. (Fixed portions including this one are represented by symbols *.)

Standing cuffs B are formed at the opposite sides of the disposable diaper so as to stand freely around the wearer's legs by projecting toward the wearer. The standing cuff B is formed with a standing sheet 4, which is continuous in the substantially lateral direction, and two kinds of stretching members; stretching members for contacting and stretching members for standing. There are suitable numbers of, or in this embodiment two stretching members 5A, 5A for contacting and suitable number of, or in this embodiment three stretching members 5B, 5B, 5B for standing. These stretching members are formed from e.g. strands of rubber, belts of rubber. The reference numeral 7 designates a tape-tab as attachment means. The reference WB designates a standing cuff for the wearer's waist for constraining back-leakage for the wearer's waist. This standing cuff WB has, at its distal edge, stretching members 7A, 7A for contacting and has, at its base line side, stretching members 7B, 7B, 7B for standing.

Further, the standing cuff B is made double by folding the inside of the standing sheet 4 inwardly. The stretching members 5A, 5A for contacting and the stretching members 5B, 5B, 5B for standing are fixed with e.g. hot melt adhesive and included in the standing cuff B. In this embodiment, a folding line defines the distal edge E1.

The laterally outboard portion of the internal side of the double standing sheet 4 is fixed to the surface of the liquid impervious sheet 2 with e.g. hot melt adhesive with the fixation starting from an edge of the liquid pervious sheet 1.

As a result, the fixation starting edge where the internal side of the double standing sheet 4 is fixed to the liquid pervious sheet 1 defines the base line E2 from which each standing cuff B stands. In the leg portion of the diaper within the laterally inboard portion with respect to this base line E2, the standing sheet 4 is not fixed to the diaper body but stands freely so as to form portion Z.

The portion Z of the standing cuff B for the wearer's leg has the lateral length L preferably at least 10 mm, particularly 30 mm to 80 mm for a diaper for adults.

Now, referring to FIG. 5, at the longitudinally front and back ends of the diaper, the relation between the standing sheet 4 and other diaper elements in fixing will be stated. The front and back ends of the portion Z of the standing sheet 4 are fixed to the wearer's side surface of the diaper. Concretely, in this embodiment, the back end is fixed to a backside flap WB for constraining back-leakage and to the liquid pervious top sheet 1. On the other hand, the front end is fixed directly to the liquid pervious top sheet 1 since a flap is not provided at the front end of the diaper with hot melt adhesive.

In FIG. 5, fixed portions F, F between the standing cuff B and the diaper body with hot melt adhesive are represented by dots. As seen from this figure, in the front end-side of the diaper, the upper fixed portion F initiates from an upper line f1 in the distal edge E1-side of the portion Z and from a lower line f2 in the proximal edge E2-side of the portion Z. The upper line f1 locates closer to the front end of the diaper than the lower line f2. On the other hand, in the back end-side of the diaper, the lower fixed portion F initiates from single line f3. This line f3 is parallel to the back end of the diaper. This line f3 is not divided into two parts having the above relation like f1 and f2.

In such configuration, the stretching members 5A, 5A for contacting extend in the vicinity of the distal edge E1 of the standing cuff B. On the other hand, the stretching members 5B, 5B, 5B for standing extend in the vicinity of the base line E2 for the portion Z of the standing cuff B.

The stretching members 5A, 5A for contacting are fixed, in the stretched state, to the standing sheet 4 with hot melt adhesive so that the distance formed between f1 and f3 is contracted. On the other hand, the stretching members 5B, 5B, 5B for standing are fixed, in the stretched state, to the standing sheet 4 with hot melt adhesive so that the distance formed between f2 and f3 is contracted. In this connection, these stretching members 5A, 5A and 5B, 5B, 5B are configured so that the effective stretching length of the stretching members 5B, 5B, 5B for standing is shorter than that of the stretching members 5A, 5A for contacting.

Figure 6A:
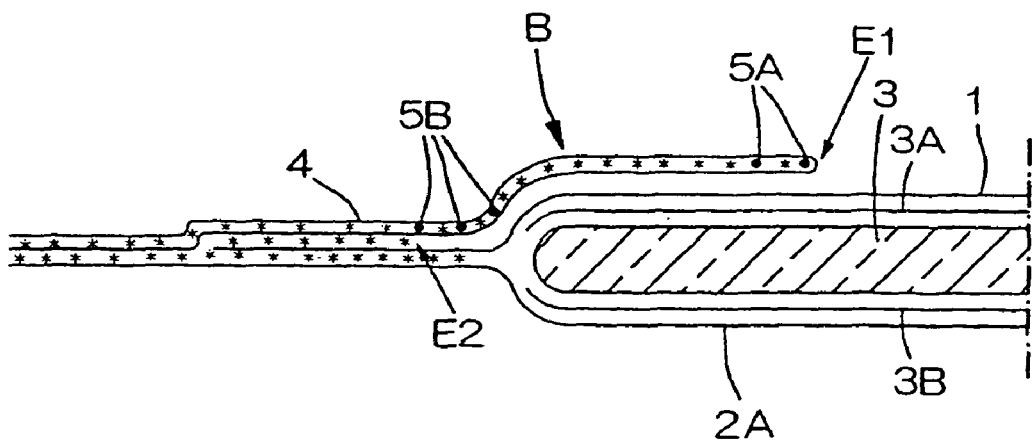
FIGS. 6A and 6B are sectional views taken on line of FIG. 5 when the diaper is in its stretched state and wearing state, respectively.
Figure 6B:
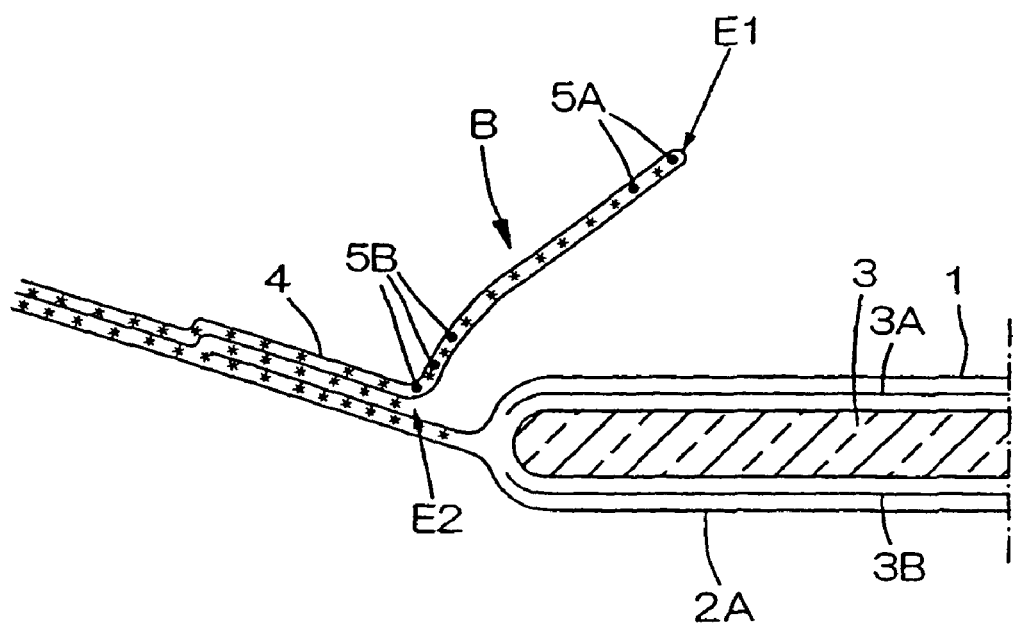
Figure 7:
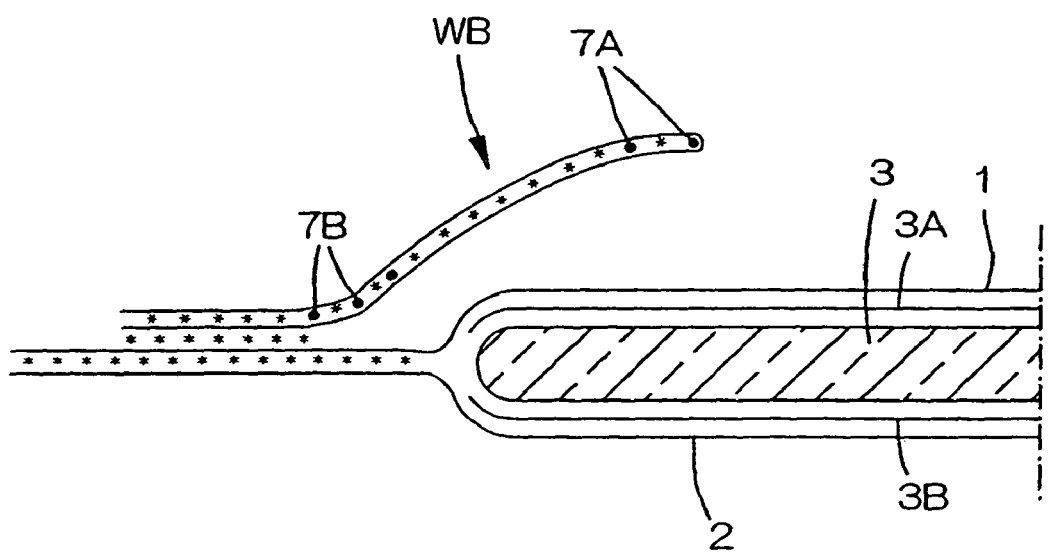
FIG. 7 is a sectional view taken on line IV-IV of FIG. 5.

In FIG. 6A, the diaper is in the state of longitudinally stretched. Actually, when the diaper is applied to the wearer as shown in FIG. 6B, it defines a boat-form in the longitudinal direction. Further, contracting force is generated by the stretching members 5A, 5A and 5B, 5B, 5B. Therefore, during the use of the diaper, in its leg portion, the standing cuff B stands through the means of application of the above contracting force by the stretching members 5A, 5A and 5B, 5B, 5B. On the other hand, in its front end and back end, it keeps the state shown in FIG. 6.

In this case, the side flap is deformed and lifted. At the same time, the absorbent core 3 is slightly deformed and lifted. Thus, a deep pocket space is formed in the diaper.

In addition, in such lifted state, the large contracting force by the stretching members 5B, 5B, 5B for standing is applied to the standing cuff B itself. Therefore, the standing cuff B is not able to stand in the substantially vertical direction. At the same time, even if the contracting force by the stretching member 5A, 5A for contacting is small, it is sure that the standing cuff B is able to stand. Precisely, in spite of the small contracting force by the stretching member 5A, 5A for contacting, thanks to the large contracting force by the stretching member 5B, 5B, 5B for standing, the standing ability of the standing cuff B can be attained. In addition, because of the small contracting force by the stretching member 5A, 5A for contacting, strong pressure is not applied to the wearer's skin from the standing cuff B.

Now, the conceptual standing manner of the standing cuff will be stated, referring to FIGS. 9A and 9B. The effective stretching length ESL X of the stretching members 5A, 5A for contacting is long and their contracting force is small, while the effective stretching length ESL Y of the stretching members 5B, 5B, 5B for standing is short and their contracting force is large. Accordingly, the contracting force toward the longitudinal centerline of the diaper applied on the base line E2 is larger than that applied on the distal edge. Hence, in the side view, the standing cuff of the diaper stands so as to form a shape something like a sector in its freely contracted state as shown in FIG. 9A. As a result, during the use of the diaper, the distal edge of the standing cuff B, at its front and back endsides, is brought into contact with low pressure, while at its laterally central portion, with relatively high pressure, as shown in FIG. 9B. At the same time, the standing cuff B is brought into contact with the wearer's leg so that the distal edge of the standing cuff B, at its front end and back end, does not stand vertically, while at its laterally central portion, stands almost vertically. In the conventional diaper, sideleakage tends to be caused at the longitudinally central portion of the distal edge of the standing cuff B. However, in the present embodiment, the problem of such side-leakage may be coped with the above configuration of the standing cuff.

Figure 10:
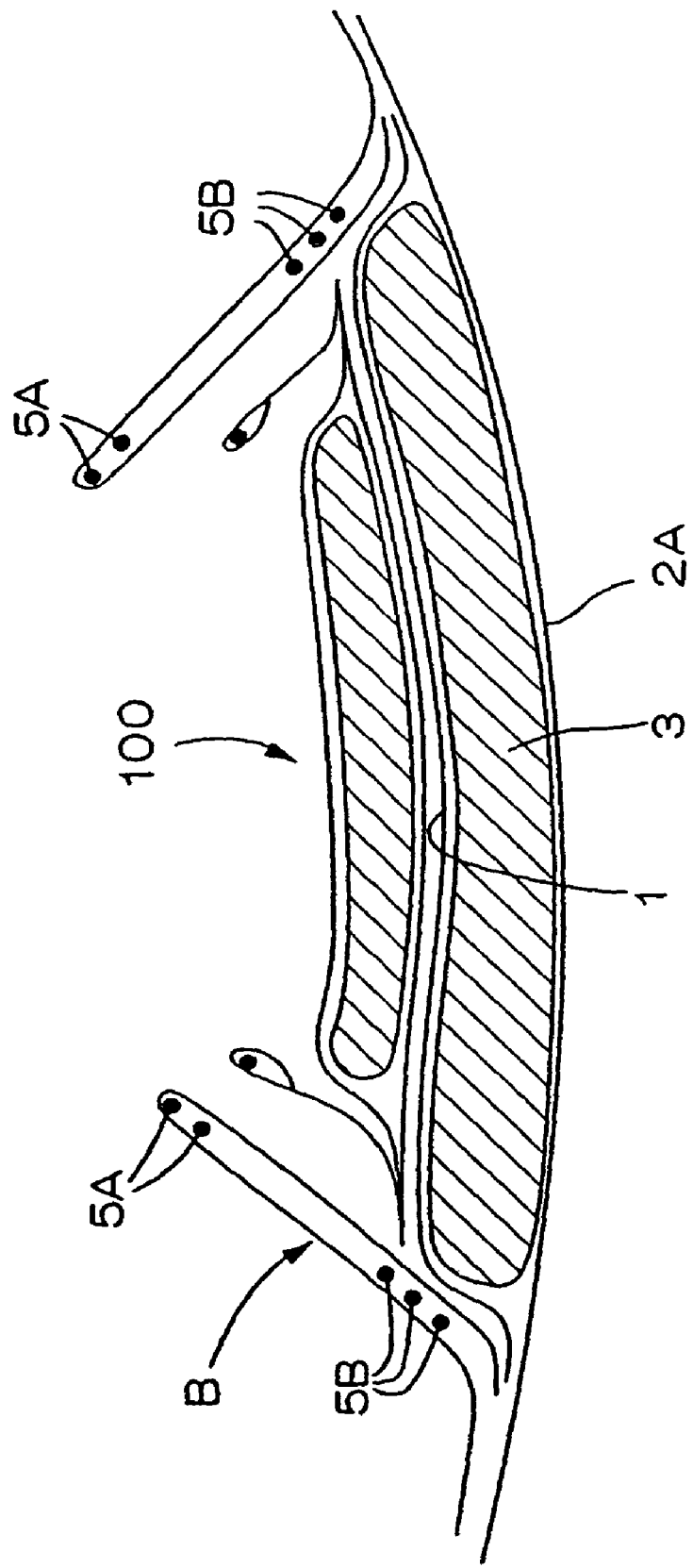
FIG. 10 is a laterally sectional view of a disposable diaper provided with a complementary pad.

Accordingly, in the present embodiment, it is clear that the standing cuff B is able to surely stand. Therefore, when the complementary pad 100 is provided so as to superpose on the wearer's side of the original diaper as shown in FIG. 10, the standing cuff B surely encloses the complementary pad 100 without lying and bending back.

Figure 8A:
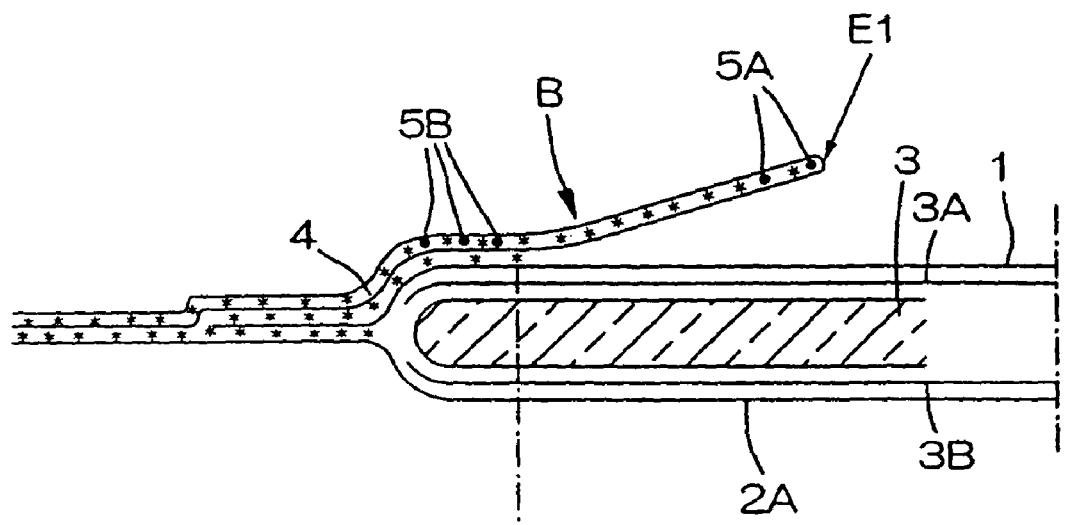
FIGS. 8A and 8B are sectional views taken on line V-V and line VI-VI of FIG. 5, respectively.
Figure 8B:
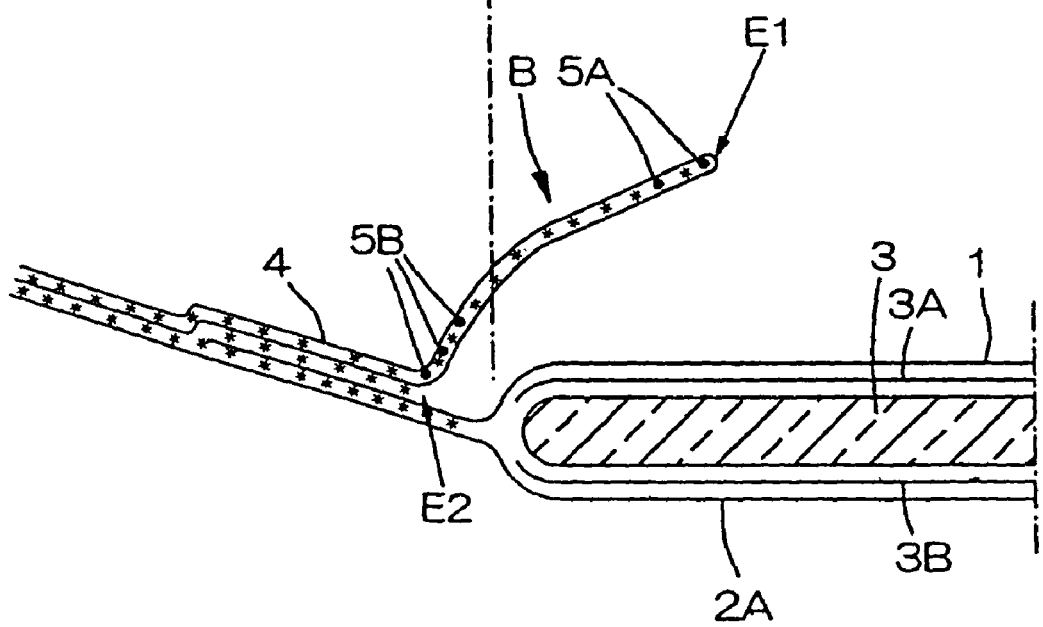

As stated before referring to FIG. 5, the upper fixed portion F, which is located at the front end-side, has the specified shape. This means that fixing manner of the standing cuff B to the diaper body is designed as follows. As shown in FIG. 8, in the front end-side portion, the distal edge of the standing cuff B stands with a decreased height by the upper fixed portion F. The base line E2 for the standing cuff B is also constrained in the front end-side portion by the upper fixed portion F. On the other hand, since there is no fixed portion F in the longitudinally central portion 4B, the standing cuff B will stand with the sufficient height by means of the stretching members 5B, 5B, 5B for standing. However, the distal edge E1 of the standing cuff B is constrained so as not to stand fully by the standing of the standing cuff B with the decreased height in the front end-side portion. Therefore, the standing cuff B stands in the longitudinally central portion with an externally convex shape at its middle portion as shown in FIG. 8B. Thus, a pocket space is formed between the opposite standing cuffs B, B of the diaper. As a result, the complementary pad 100 can be surely enclosed.

Figure 11:
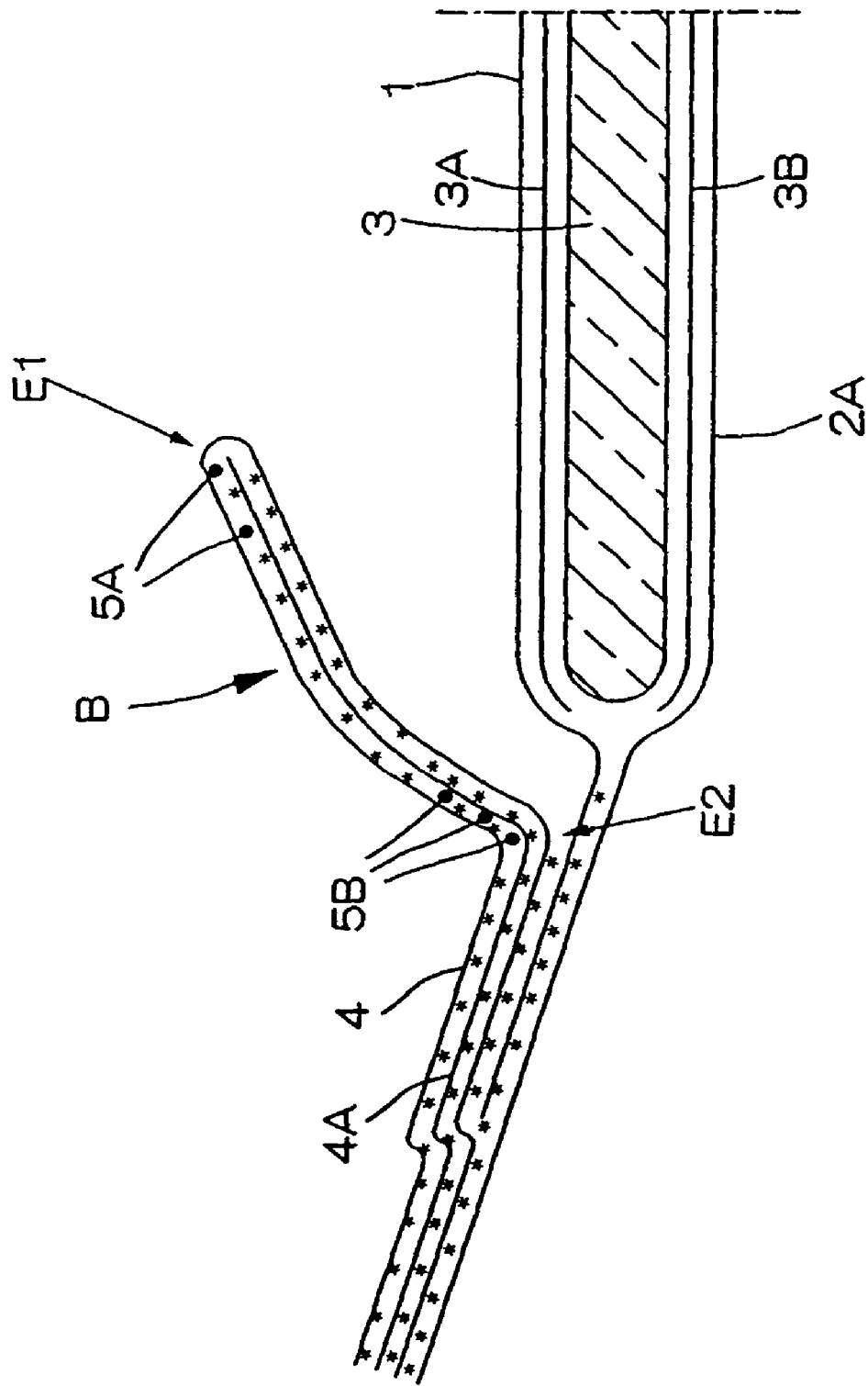
FIG. 11 is a laterally sectional view of disposable diaper alternative embodiment.
Figure 12:
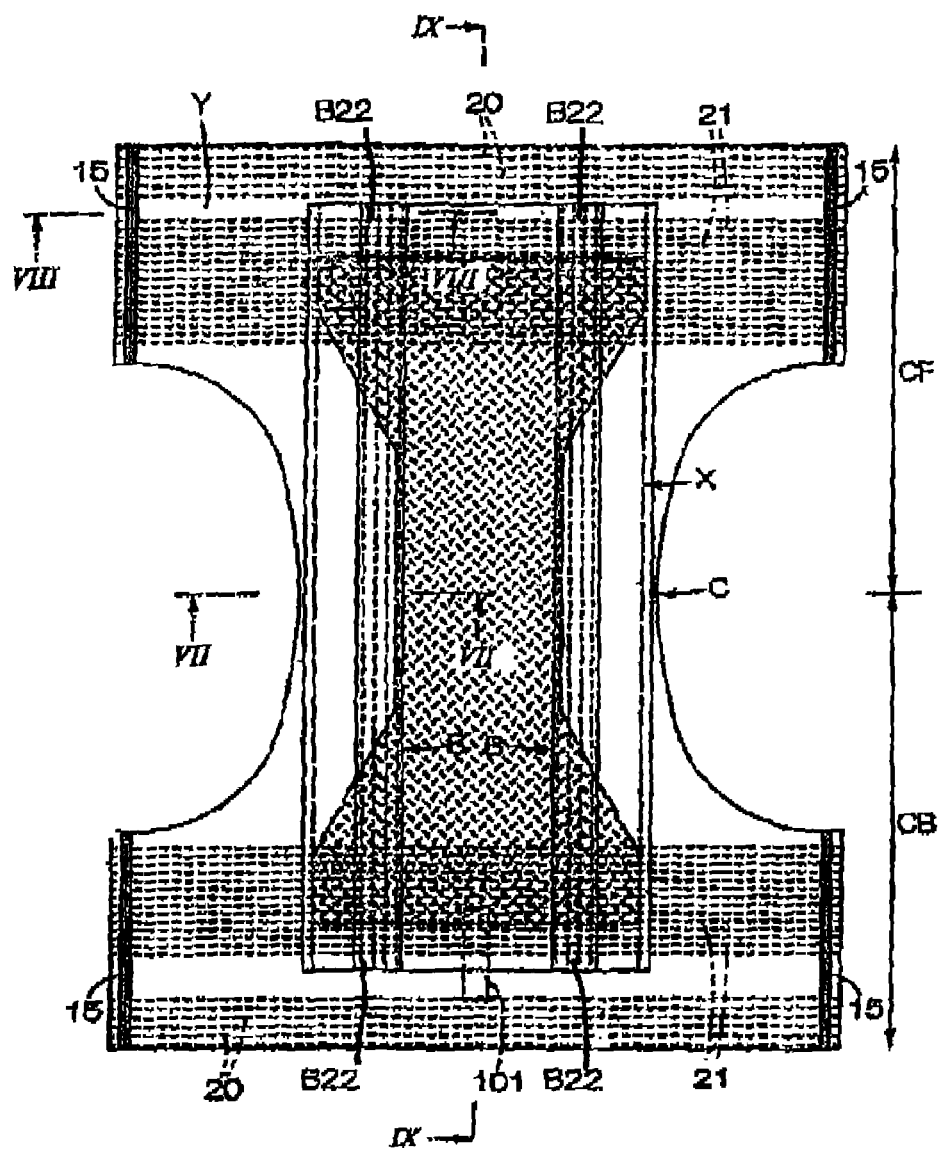
FIG. 12 is a plan view of a disposable diaper pant-type embodiment, when the diaper is in its stretched state.

As the material of the standing sheet, a material such as breathable and liquid impervious plastic film or non-woven fabric, which is treated with silicone so as to have water repellency, can be used. As shown in FIG. 11, a water proof sheet 4A which is manufactured from a plastic film or the like is preferably disposed between the non woven fabrics with or without water repellency in order to surely prevent the liquid permeation. As the non-woven fabric, a polypropylene nonwoven fabric, which is manufactured with a melt blown method, is more preferable. The standing sheet with the thickness of 5 g/m$^2$ to 30 g/m$^2$ defined by the basis weight is adhered to be formed like a pouch and the pouched edge defines the distal edge E1. The stretching member is formed from strand of natural rubber, synthetic rubber, polyurethane or the like. The stretching members may be in the form of strands or a belt. In this embodiment, the standing cuff B is able to stand in the substantially vertical direction through the means of the application of the large contracting force by the stretching members 5B, 5B. Concretely, as the stretching members 5A, 5A for contacting, two strands of 560-denier urethane extend for the longitudinal distance of 650 under the elongation of 280%. On the other hand, as the stretching members 5B, 5B, 5B for standing, three strands of 560-denier urethane extend for the longitudinal distance of 420 mm under the elongation of 280% at intervals of about 5 mm.

When a diaper with tape-tab fasteners is applied to a wearer, in a standing cuff B, the elongation of a stretching member 5A for contacting varies between 60% and 150%, while that of a stretching member 5B for standing varies also between 60% and 150%. Then, the stretching stress of the stretching member 5A for contacting is 0.29 N to 1 N, preferably, 0.39 N to 0.90 N, while that of the stretching member 5B for standing is 0.39 N to 1.50 N, preferably 0.49 N to 1.38 N. In these situation, the wearer does not feel the pressure and a gap is not formed between the leg portion of the diaper and the wearer's leg, resulting in reliable protection against the leakage. In the above embodiment, when the elongation of the stretching member 5A for contacting is 60% to 150%, its stretching stress is 0.39 N to 0.90 N, and when the elongation of the stretching member 5B for standing is 60% to 150%, its stretching stress is 0.49 N to 1.38 N.

In addition to the diaper, the absorbent article of the present invention is applied to a sanitary napkin. Taking account of this, it is preferable that when the elongation of the portion provided with the stretching member for contacting is 60% to 150%, its stretching stress is 0.10 N to 1.30 N (per the width of 15 mm and the length of 100 mm), and that when the elongation of the portion provided with the stretching member for standing is 60% to 150%, its stretching stress is 0.20 N to 2.00 N (per the width of 15 mm and the length of 100 mm).

In the above embodiment, the standing cuff WB for the wearer's waist is provided on only the back end-side portion. However, the standing cuff WB for the wearer's waist may be provided on also the front end-side portion. Alternatively, the standing cuff WB for the wearer's waist may not be provided.

Further, if desired, stretching members may longitudinally extend on opposite side flaps, which laterally extend beyond the standing cuffs B, in order to attain gasketing cuffs.

The Fourth Embodiment

FIGS. 12 to 17

As shown in FIGS. 12-17, a pant-type disposable diaper in accordance with the fourth embodiment comprises a flexible overall sheet Y and an absorbent main body X fixed to the internal side surface of the overall sheet Y. This absorbent main body X extends to the front end and back end of the diaper (longitudinally) from a crotch zone corresponding to the wearer's crotch. The reference numeral 101 designates a so-called after-treatment tape, which is used for sealing a rolled pack of used diaper and which is provided on the back surface of the overall sheet Y.

The overall sheet Y is manufactured by laminating and fixing two breathable and water repellant non-woven fabrics. Then, in the production process of this diaper, after superposing step of the overall sheet Y and the absorbent main body X, the last step is carried out. In this last step, the longitudinal opposite side edges of the front half CF and those of the back half CB are totally joined with joining means such as ultrasonic sealing or hot melt adhesive (the joined portion is designated by reference numeral 15) to thereby form an aperture around the wearer's waist and apertures around the wearer's legs.

The absorbent main body X comprises a liquid pervious top sheet 11, an absorbent structure AB, and a liquid impervious back sheet 12, which are fixed integrally with hot melt adhesive. The liquid pervious top sheet 11 is manufactured from e.g. non-woven fabric and brought into contact with the wearer's skin directly, and has the shape of rectangle. The absorbent structure AB comprises an hourglass-shaped absorbent core 13 and rectangle shaped crepe paper 14. The absorbent core 13 is manufactured mainly from flocculent pulp and has some stiffness. The rectangular crepe paper 14 surrounds the over and under surfaces of the absorbent core 13 and laterally extends beyond the side edge of the absorbent core 13 to thereby form an extended peripheral side portion. The back sheet 12 is manufactured from e.g. polyethylene plastic film and has the shape of rectangle. The back sheet 12 wraps around the absorbent structure AB from its back to the opposite side portions of its over surface. If required, a liquid pervious second sheet 115 may be disposed between the liquid pervious top sheet 11 and the crepe paper 14.

Almost all the back of the absorbent main body X is fixed to the above-said overall sheet Y with hot melt adhesive so as to be integrated each other, leaving small opposite side portions of the liquid impervious back sheet 12 unfixed to the overall sheet Y.

Standing cuffs B are formed at the opposite sides of the above absorbent main body X so as to stand around the wearer's legs by standing toward the wearer. The standing cuff B is formed with a standing sheet 40, which is continuous in the substantially lateral direction, and one stretching member or a plurality of stretching members 50, 50 . . . as shown in the Figures, which is or are formed from a strand or strands of rubber.

Further in detail, the standing cuff B is made double by folding the inside of the standing sheet 40. The stretching members 50, 50 . . . are included and fixed within the standing cuff B with e.g. hot melt adhesive. It is preferable that the standing sheets 40, which form the standing cuffs B, B, are not liquid pervious but liquid impervious or hydrophobic. Alternatively, it is also preferable that the standing sheet is treated with e.g. silicone so as to have water repellency.

The internal side of the double standing sheet 40 is fixed to the over surface of the liquid impervious back sheet 12 along its portions wraparound to the absorbent structure AB. with e.g. hot melt adhesive. The proximal edge where the internal side of the double standing sheet 40 is fixed to the liquid pervious sheet 12, defines the base line BL from which the standing cuff B stands. The laterally inboard portion with respect to this base line is not fixed to the diaper body but free therefrom. Further, this inboard portion folds back halfway so as to be divided functionally and conceptually into two portions, a standing portion B1 which stands toward the longitudinal centerline of the diaper and a surface-contacting portion B2 which bends outwardly.

Figure 13:
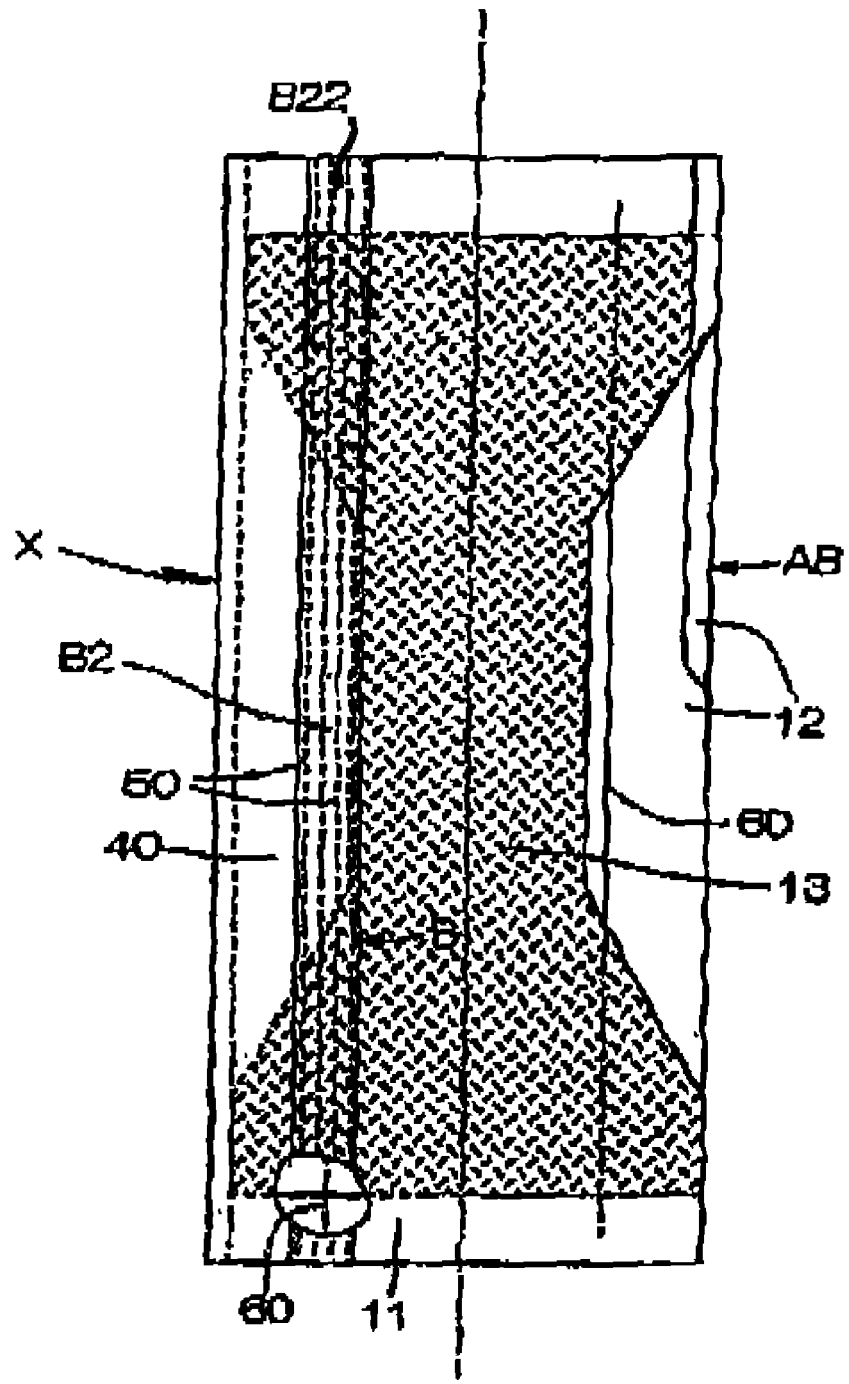
FIG. 13 is a semi cut away plan view showing its only main absorbent structure.
Figure 15:
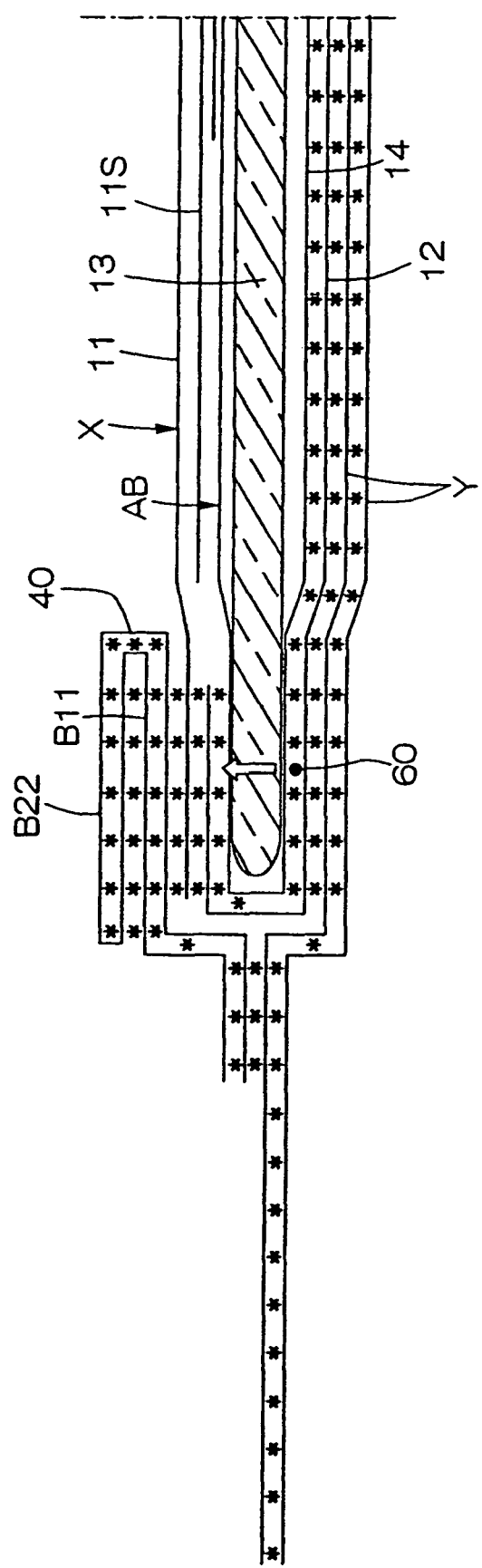
FIG. 15 is a sectional view taken on line VIII-VIII of FIG. 12.

As shown in FIGS. 13 and 15, in the front and back ends of the standing cuff B in its longitudinal direction the portion corresponding to the above-said standing portion B11 (the extension of the standing portion B1) is fixed diaper body (see FIG. 15), concretely to the external surface of the liquid pervious sheet 1, by laying the portion B11 toward the longitudinal centerline of the diaper, while the portion corresponding to the above-said surface-contacting portion B22 (the extension of the surface-contacting portion B2) being folded back and inverted is fixed to the portion corresponding to the standing portion B11 (see FIG. 15).

In a basic aspect, at least one stretching member 50 extends on the surface-contacting portion B2. Preferably, the stretching member 50 extends along the side edge of the surface-contacting portion B2. Further, it is preferable that the stretching member 50 extends also on the standing portion B1.

In the more preferable aspect, the stretching members 50. 50 . . . extend in the vicinity of the base line for the standing portion B1, in the vicinity of the distal edge of the double standing sheet, and in the vicinity of the side edge of the surface-contacting portion B2. In addition, a plurality of stretching members 50, 50 . . . preferably extend in the vicinity of the side edge of the surface-contacting portion 20 as shown.

Figure 14:
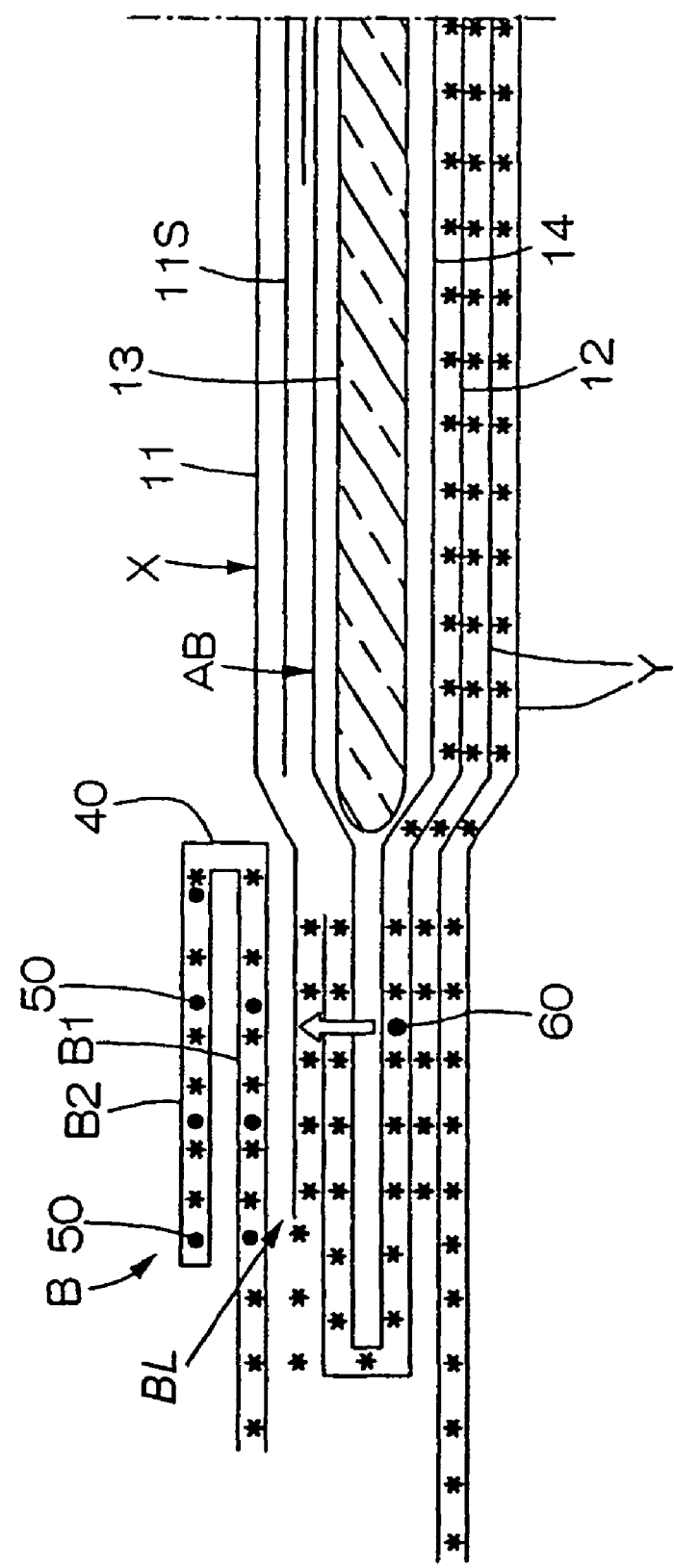
FIG. 14 is a sectional view taken on line VII-VII of FIG. 12.

Additionally, in order to improve the standing ability of the standing portion B1, a plurality of stretching members 50, 50 . . . may further extend on the standing portion B1. In FIG. 14, there are shown seven stretching members in total, three stretching members in its standing portion B1 and four stretching members in its surface-contacting portion B2.

Figure 17:
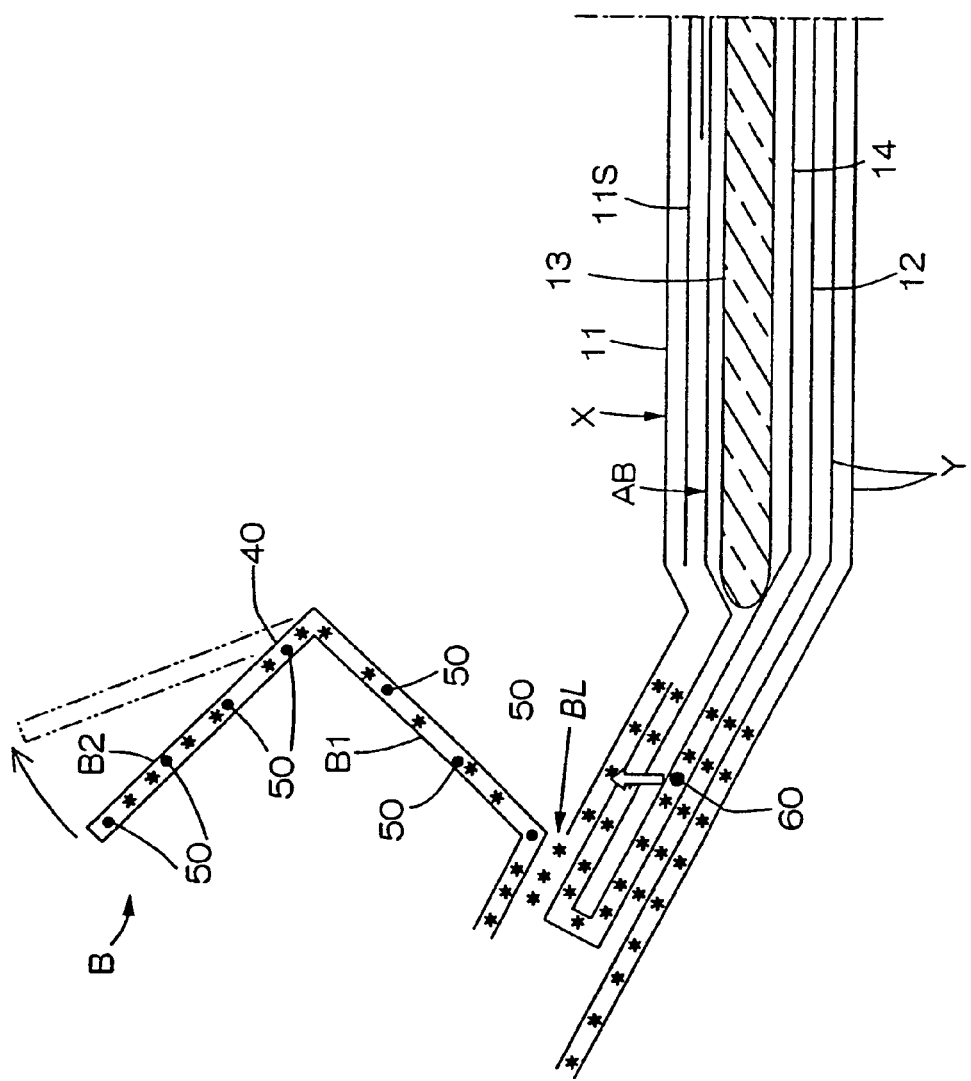
FIG. 17 is a sectional view taken on line VII-VII of FIG. 12 when the disposable diaper is in its wearing state.

In FIG. 14 and FIG. 15, the diaper is in its longitudinally stretched state. Actually, when the diaper is applied to the wearer, it defines a boat-form, while the contracting force is applied to it by means of the stretching members 50, 50 . . . . Therefore, during the use of the diaper, in its leg portion, the standing cuff B stands by means of the above contracting force as shown in FIG. 17, while in its front and back ends, it keeps the state shown in FIG. 15. In this case, the extended peripheral side portion of the absorbent main body X is deformed and lifted. At the same time, the absorbent core 3 is slightly deformed and lifted. Thus, a deep pocket space is formed in the diaper.

In addition, in such lifted state, the contracting force by the stretching members 50, 50 . . . is applied to the standing cuff B itself. Therefore, the standing portion B1 is able to stand in the substantially vertical direction. The surface-contacting portion B2 also stands vertically. However, since the portion corresponding to the surface-contacting portion B22 being folded back and inverted is fixed to the portion corresponding to the standing portion B11, vertical standing is limited and the surface-contacting portion 2B stands facing outward and keeping the standing force in the vertical direction. As a result, the surface-contacting portion B2 always fits flat around the wearer's leg.

The space formed between the standing portions B1, B1 forms a pocket space for enclosing urine and loose feces. When they are captured in the pocket space, the urine is absorbed into the absorbent core AB through the liquid pervious top sheet 11, and the solid component of the loose feces is prevented from flowing beyond the standing cuff B due to its standing portion B1, B1 as barriers. If the urine and the liquid component of the loose feces should flow beyond the distal edge of the standing portion B1, the surface-contacting portion B2 functions as a stopper against the side-leakage.

Figure 16:
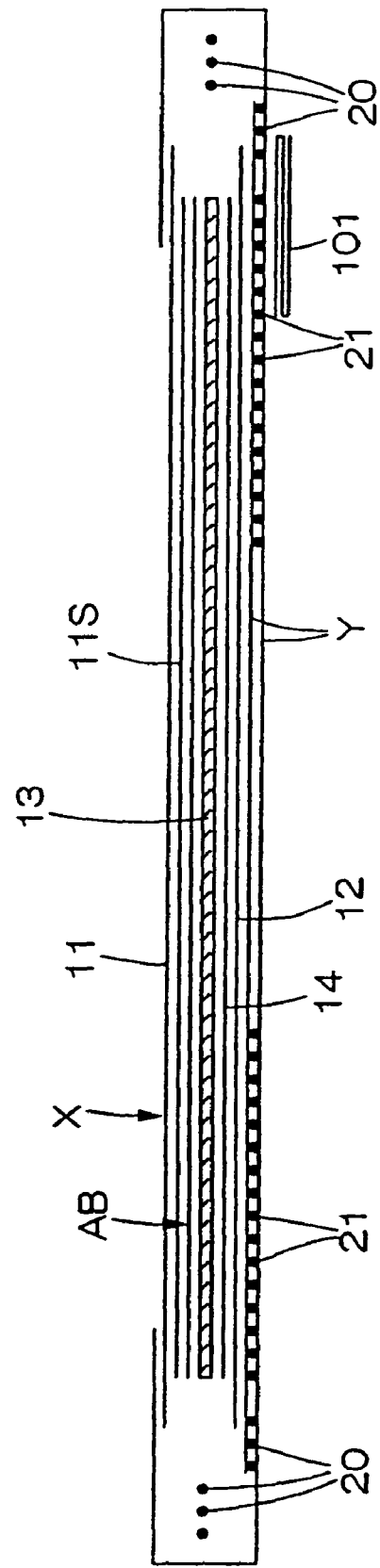
FIG. 16 is a sectional view taken on line IX-IX of FIG. 12.

As closely shown in FIG. 16, in the front half CF and back half CB, in order to improve fitting of the diaper around the wearer's waist, stretching members 20, 20 . . . for wearer's waist extend so as to be fixed between the non-woven fabrics of the overall sheet Y as well as in the portions folded back at the front and back ends of the back of the overall sheet Y. The stretching members 20, 20 . . . for wearer's waist are formed from the strands of rubber with small diameters and disposed to fix in the stretched state so as to be parallel to front end and back end of the aperture around the wearer's waist and so as to stretch with elasticity. The interval and number of the stretching members 20, 20 . . . for the wearer's waist may be determined suitably, for example, the interval is about 4 mm to 6 mm and the number is 5 to 7.

Further, in both of the front half CF and back half CB, in order to improve fitting of the diaper for the wearer's underbelly region and to prevent urine leakage from the front and back sides, stretching members 21, 21 . . . for the wearer's hips extend so as to be fixed between the non-woven fabrics of the overall sheet Y. These stretching members 21, 21 . . . are formed from the strands of rubber with small diameters and disposed to fix in the stretched state so as to be parallel to the front end and back end of the aperture around the wearer's waist for elastic stretching. The number of the stretching members 21, 21 . . . for the wearer's hips is 9 to 25. The interval of the stretching members 21, 21 . . . for the wearer's hips is the same as or smaller than that of stretching members 20, 20 . . . for the wearer's waist.

The stretching stress and outer diameter of the cross section of the rubber with small diameter for the stretching member 20 for wearer's waist are substantially the same as those of the stretching member 21 for wearer's hips. Completely identical strands of rubber may simply be used for the both stretching members, but there may be a difference, except the above-mentioned characteristics, such as difference of color. Concretely, the stretching stress of the strand of rubber with small diameter is preferably 4 g to 17 g, more preferably 5 g to 10 g under the elongation of 150%, while the outer diameter of the cross section of the strand of rubber is preferably 100 µm to 350 µm, more preferably 120 µm to 270 µm.

In this embodiment, as stated above, the stretching members 50, 50 . . . which are disposed on the standing cuffs B, B curls the absorbent main body X inwardly. Accordingly, the synergy of such curling action by the stretching members 50, 50 . . . and fitting (tightening) action for the wearer's hips by the stretching members 21, 21 . . . causes the apertures around the wearer's legs to be contracted. Further, side-leakage can be protected surely with only the standing cuffs B, B. In the third embodiment stated below, in order to contract the apertures around the wearer's legs, stretching members extend along the apertures around the wearer's legs toward the crotch zone 4. However, in this fourth embodiment, such stretching members are not required.

(Stretching Member for Lifting)

In this fourth embodiment, at the opposite sides of the absorbent structure AB and within the laterally inboard portion with respect to the base line for the standing cuff, stretching members 60 for lifting are fixed in the stretched state.

In the embodiment shown in FIGS. 14, 15 and 17, the stretching members 60 for lifting are respectively disposed between the liquid impervious back sheet 12 and the absorbent structure AB. Further, in a plane view, as shown in FIG. 13, in each leg portion of the diaper, the stretching member 60 for lifting is not superposed on the narrow portion of the absorbent core 13, while in front end and back end of the diaper, it is superposed on the laterally extended portions of the absorbent core 13. In other words, the stretching member 60 is not superposed on the narrowest width portion of the absorbent core 13, while the member is superposed on the widest width portion of the core.

By providing such stretching members 60 for lifting, the above mentioned operation and effect can be obtained.

The explanation will be given again, referring to drawings, particularly to FIG. 13, which shows typical embodiment. Precisely, as stated above, at the opposite sides of the absorbent structure AB within the laterally inboard portion with respect to the base line for the standing cuff, stretching members 60 for lifting are fixed in the stretched state. During the use of the diaper, as shown in FIG. 17, by means of the contraction force by the stretching members 60 for lifting (the direction of each force is shown in a white arrow), the opposite sides of the absorbent structure AB are deformed so as to stand toward the wearer. In addition to this standing of the opposite sides of the absorbent structure AB, the standing cuffs B stand from the base lines, which are disposed laterally outboard with respect to the stretching members 60 for lifting. This means that the height of diaper's standing is high, resulting in a deep pocket space and an improved fitting with the wearer's skin. As a result, by utilizing only standing cuffs B, the side-leakage can surely be constrained.

The Fifth, Sixth and Seventh Embodiments

FIGS. 18 to 24

Figure 18:
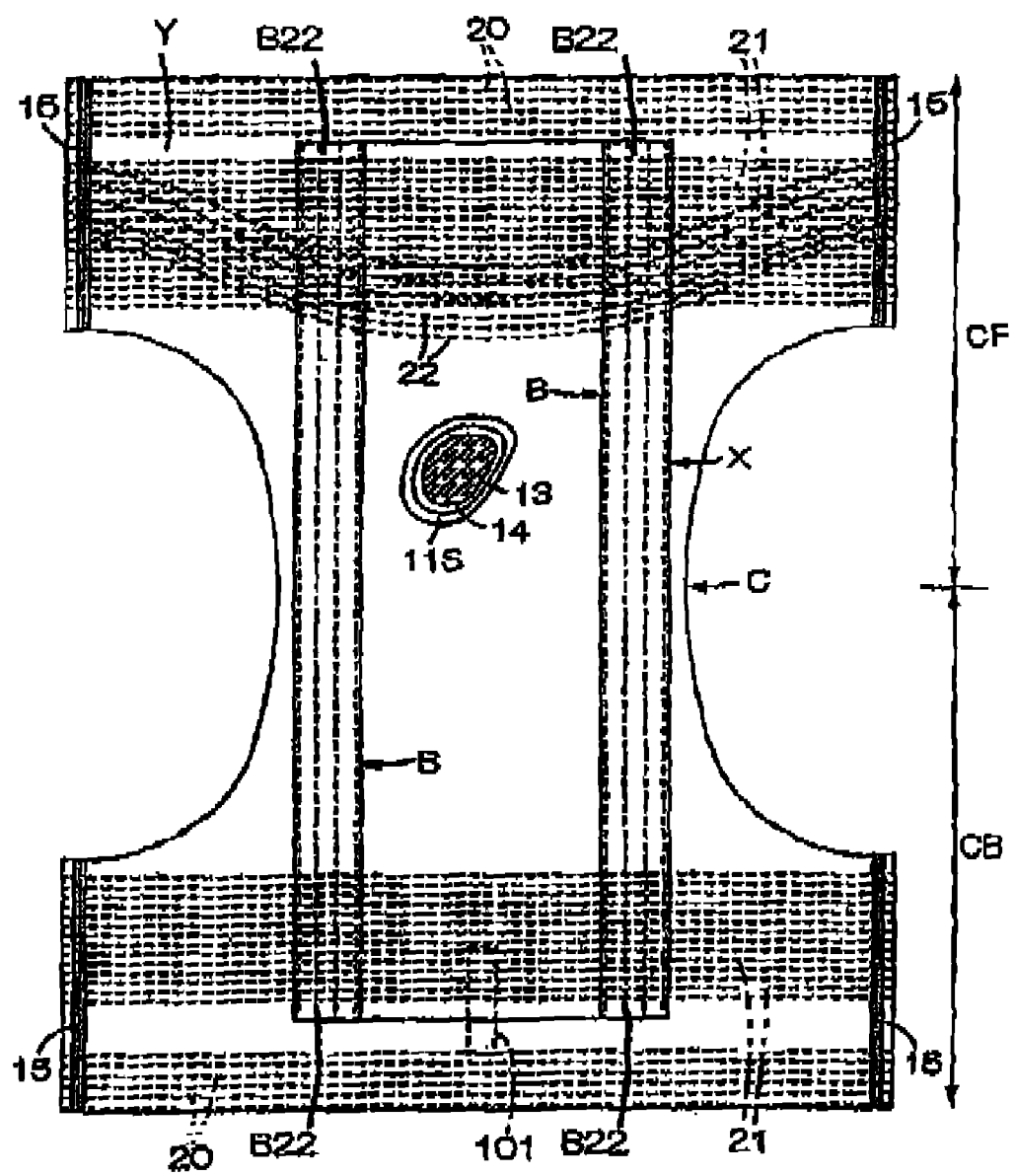
FIG. 18 is a plan view of a disposable diaper alternative pant-type embodiment having portions cut away, when the diaper is in its stretched state.

In the fifth embodiment, as shown in FIG. 18, in the front half of the diaper, stretching members 22 for fitting are further fixed between the non-woven fabrics of the overall sheet 1. Each stretching member 22 for fitting made of strand of rubber extends between the opposite side edges of the front half with the pattern of a downwardly swelling shape. This shape is toward the crotch zone, but without reaching there. In the example shown in the Figure, about a half of the swelling portion of the stretching members 22 for fitting are superposed on the stretching members 21 for the wearer's hips, while the other half swells below the bottom of the stretching member 21 for the wearer's hips. In the back half of the diaper, the stretching members for fitting are not provided.

By providing such stretching members for fitting, the diaper is lifted from its underbelly area, which corresponds to the wearer's underbelly region, to its crotch zone, so that the diaper gives proper fitting around the wearer's hips, although in the above first embodiment, by means of the stretching members 21, 21 . . . for the wearer's hips, the diaper gives sufficiently fitting around the wearer's hips.

Figure 19:
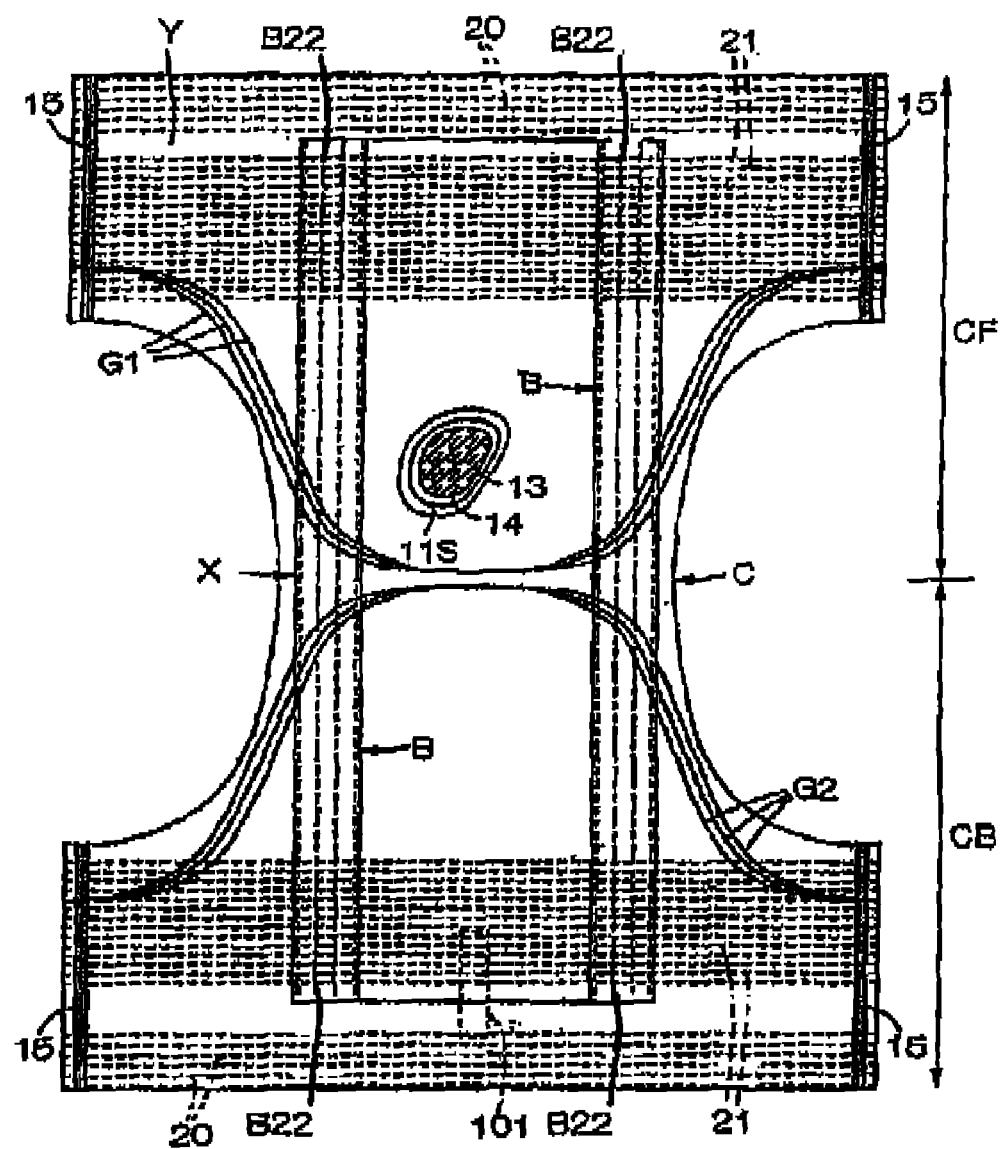
FIG. 19 is a plan view of disposable diaper further alternative embodiment having portions cut away, when the diaper is in its stretched state.

In the sixth embodiment, as shown in FIG. 19, in the front half CF and the back half CB, one or a plurality of (in the example shown in the Figure, three) stretching members G1, G1, G1 and G2, G2, G2 for legs made of strands of rubber are disposed between the non-woven fabrics of the overall sheet Y, respectively in order to contract the leg portions of the diaper. Specifically, the stretching members G1 in the front half CF are fixed so as to be continuous from a left hip portion, the left leg portion, the crotch zone C, the right leg portion and a right hip portion. By these stretching members G1, G1, G1 and G2, G2, G2, the right leg portion and left leg portion may be gathered, respectively, resulting in high protection against the leakage from the right and left leg portions.

Figure 20:
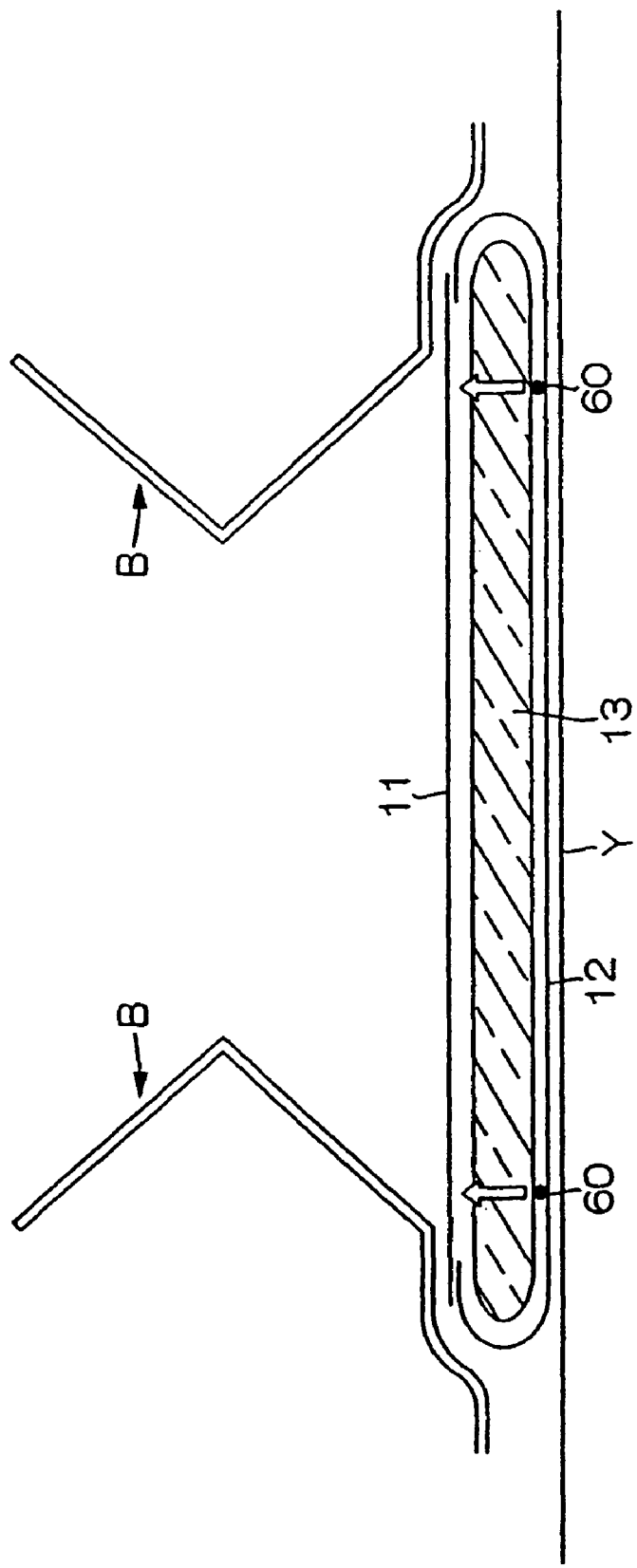
FIG. 20 is a laterally sectional schematic view showing conceptually the location of a stretching member for lifting in a disposable diaper embodiment.
Figure 21:
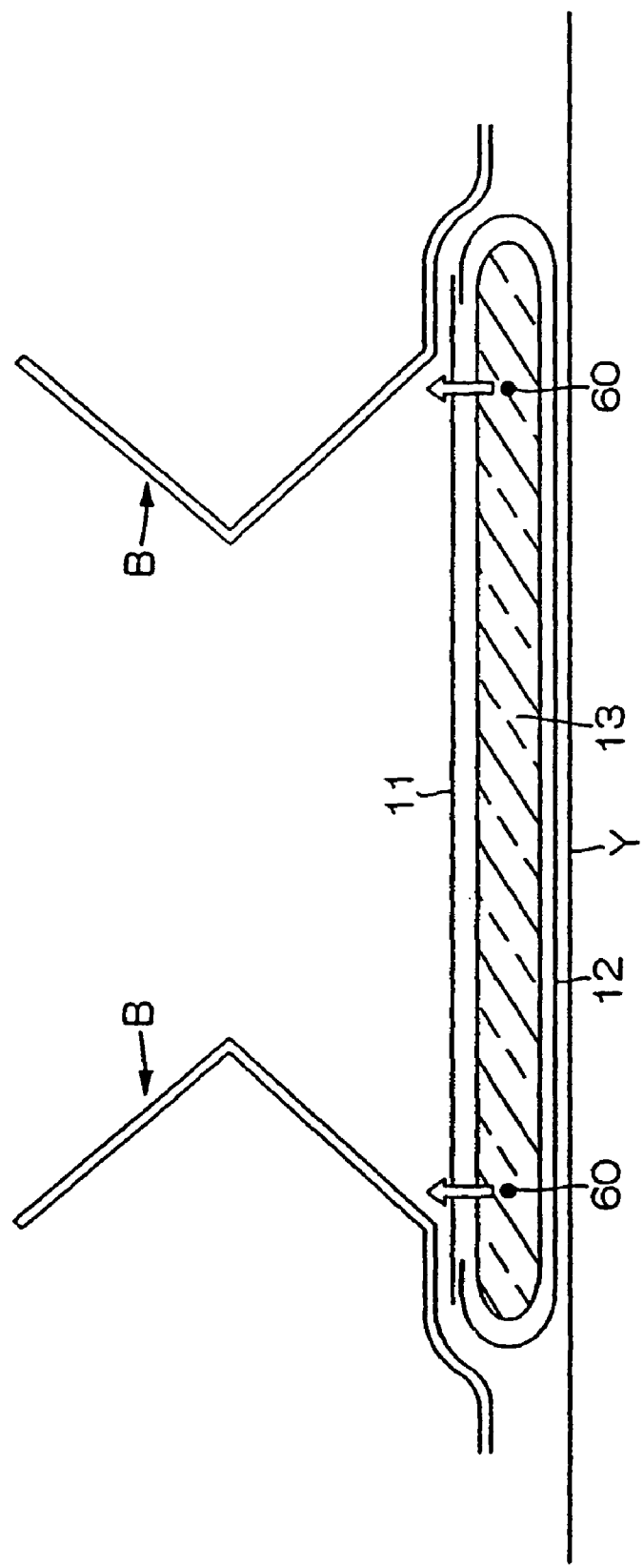
FIG. 21 is a laterally sectional schematic view showing conceptually the location of a stretching member for lifting in a disposable diaper alternative embodiment.
Figure 22:
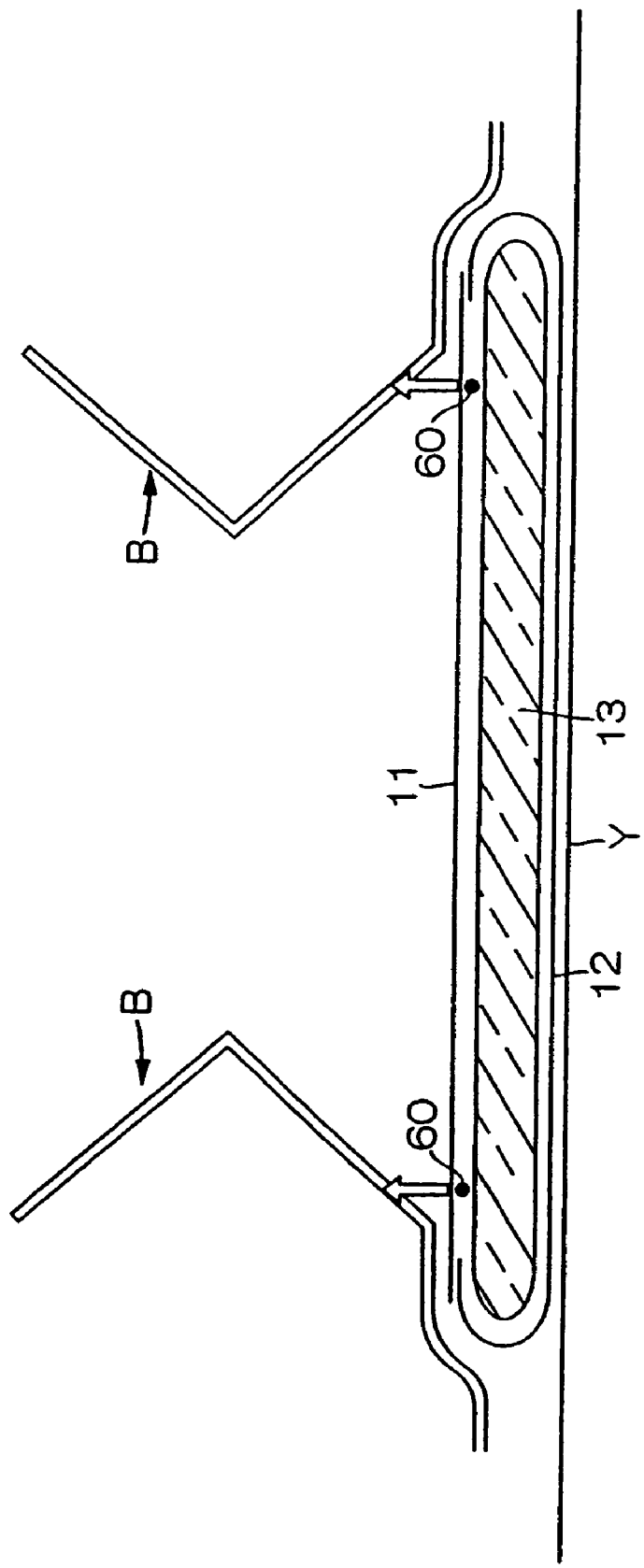
FIG. 22 is a laterally sectional schematic view showing conceptually the location of a stretching member for lifting in a disposable diaper further alternative embodiment.

In the seventh embodiment, as conceptually shown in FIG. 20, the stretching members 60, 60 for lifting are disposed between the liquid impervious back sheet 12 and the absorbent structure AB. Alternatively, as conceptually shown in FIG. 21, stretching members 60, 60 for lifting may be disposed in the absorbent core 13 in its thickness direction, and as conceptually shown in FIG. 22, stretching members 60, 60 for lifting may be disposed between the liquid pervious top sheet 11 and the absorbent structure AB so as to be fixed to at least one of them.

Figure 23:
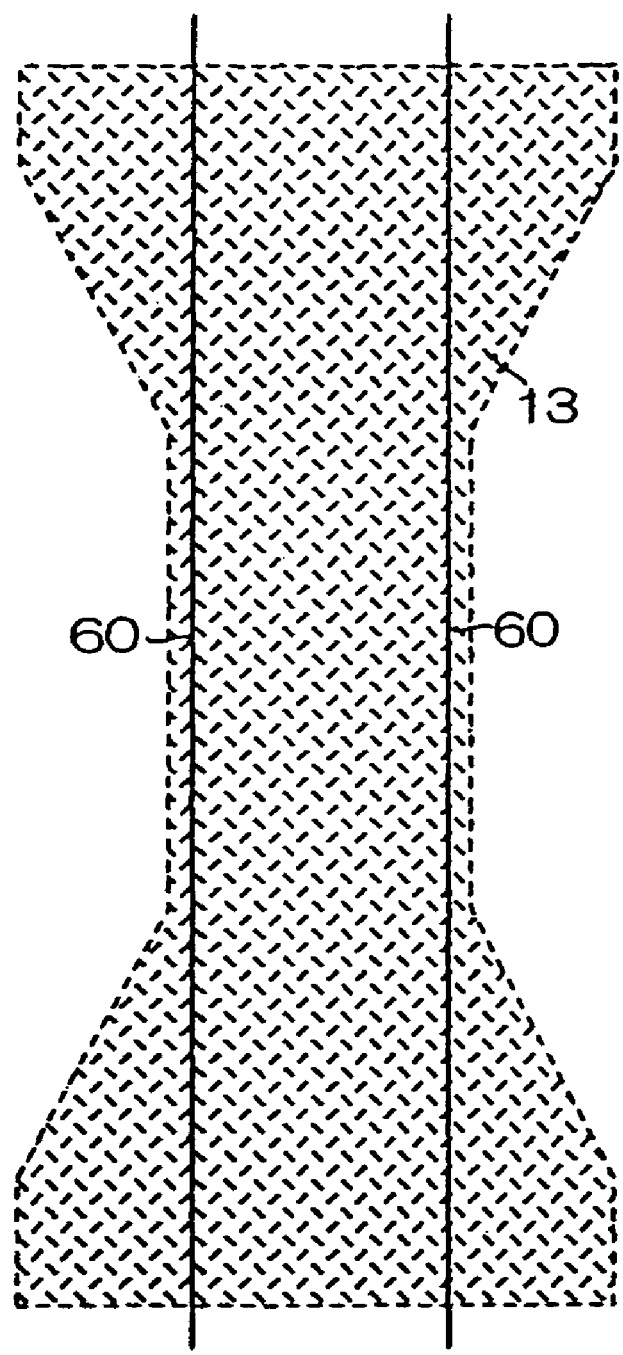
FIG. 23 is a schematic plan view showing an alternative relation between an absorbent core and a stretching member for lifting in a disposable diaper.
Figure 24:
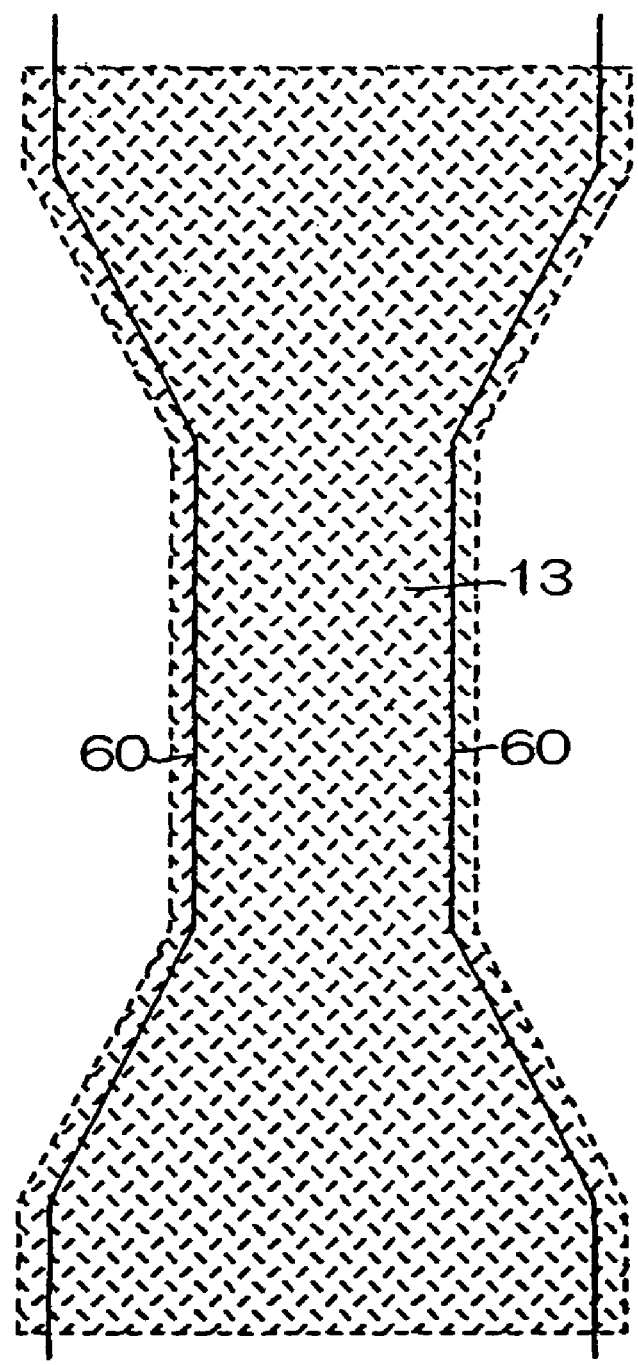
FIG. 24 is a schematic plan view showing a further alternative relation between an absorbent core and a stretching member for lifting in a disposable diaper.

Referring to the position of the stretching member 60 for lifting in the plan view, as shown in FIG. 23, the stretching member 60 for lifting may be superposed in its longitudinal direction to the absorbent core 13. As shown in FIG. 24, the stretching member 60 for lifting may extend along the side edge of the absorbent core 13. Alternatively, although not shown, the following position is possible. When the absorbent structure AB comprises the absorbent core 13 with a rectangle shape and wrapped with the rectangle shaped crepe paper 14 having the width being larger than that of the absorbent core, the stretching members 60, 60 may be disposed on only the flap portions of the crepe paper 14.

In the above embodiments, the base line for each standing cuff B is disposed on the absorbent structure AB. However, the base line may be disposed directly on the absorbent core 13 or may be apart from the absorbent structure AB, on a flap of an article, for example, on the overall sheet Y. The base line for each standing cuff B may be apart from the absorbent structure AB and disposed on the overall sheet Y, which is formed to be liquid impervious sheet such as polyethylene.

The Eighth Embodiment

FIGS. 25 to 28

Figure 25:
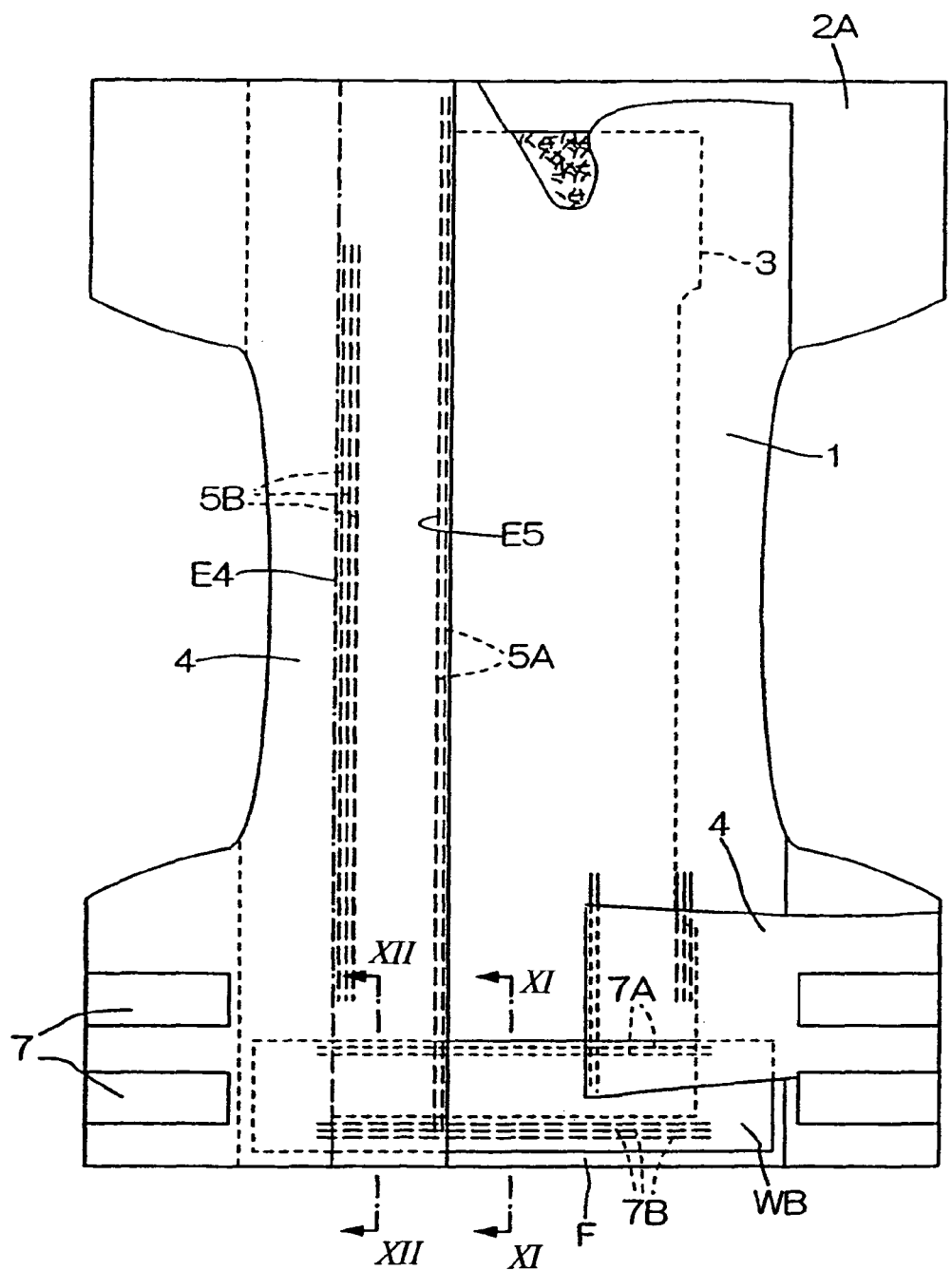
FIG. 25 is a plan view of a disposable diaper, which has a standing cuff for the wearer's waist, having portions cut away.

In the eighth embodiment, as shown in FIGS. 25 and 26, a standing cuff WB for the wearer's waist is provided at the back end of a disposable diaper so as to stand freely by projecting toward the wearer. The explanation about the configuration of other elements is obviated, since it was already given referring to FIG. 5.

The standing cuff WB for the wearer's waist is formed with a standing sheet 6, suitable number of, in this embodiment two stretching members 7A, 7A for contacting and suitable number of, in this embodiment three stretching members 7B, 7B, 7B for standing. These stretching members are also formed with e.g. strands of rubber or belts of rubber. In this eighth embodiment, the standing cuff WB for the wearer's waist is provided on only the back end of the diaper, but a further standing cuff may be provided on the front end.

The standing cuff WB is made double by folding the inside of the standing sheet 6 inwardly. The stretching members 7A, 7A for contacting and the stretching members 7B, 7B, 7B for standing are included and fixed therein with e.g. hot melt adhesive. In this embodiment, one folding line defines the distal edge E1 and another folding line defines the back end edge E3 in the longitudinal direction. Both end portions of the standing sheet 6 in the longitudinal direction are superposed each other in the vicinity of the stretching members 7B, 7B, 7B for standing so as to form a double portion (but this double portion is not shown).

Figure 27:
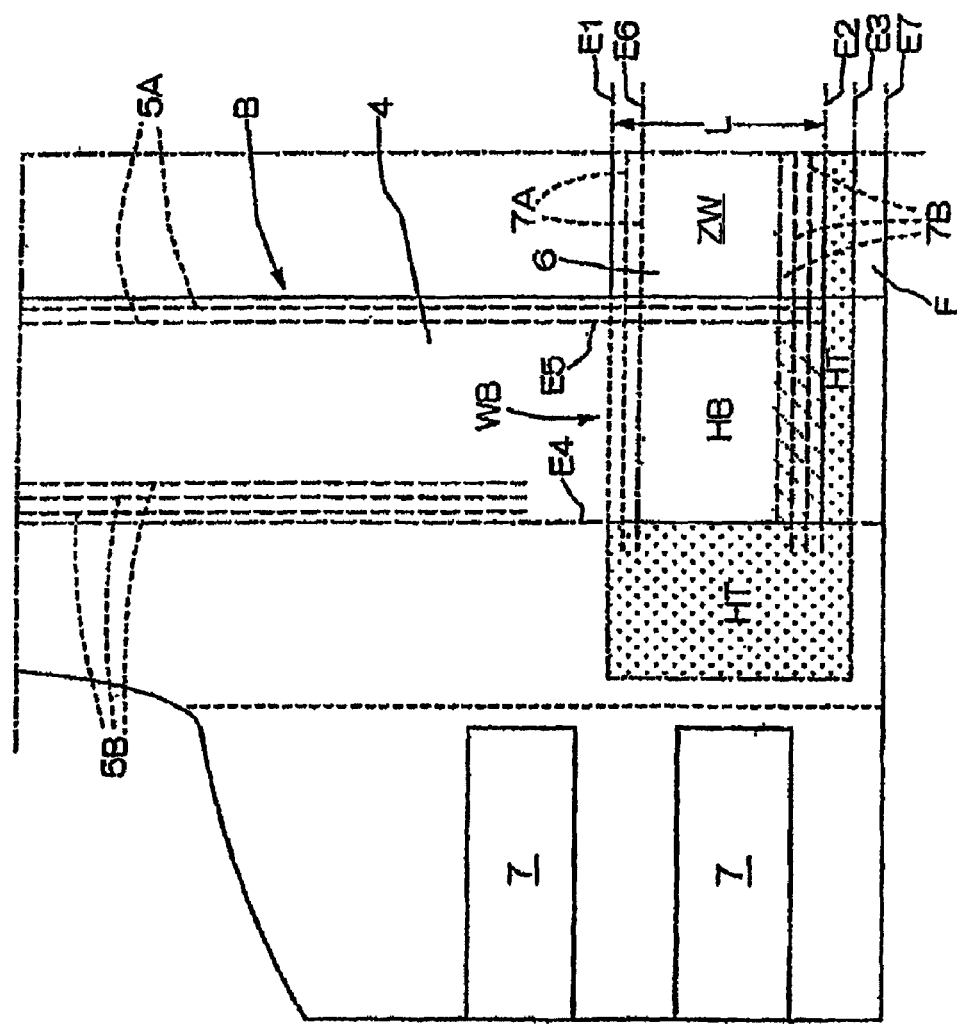
FIG. 27 is an enlarged view showing the securing of standing cuff for the wearer's waist.

In the longitudinally outboard portion of the internal side of the double standing sheet 6 is fixed to the longitudinally extended back end portion of the liquid pervious top sheet 1 with e.g. hot melt adhesive. In this embodiment, the liquid pervious top sheet 1 longitudinally extends beyond the back end of the absorbent core 3 so as to form a waist flap F. The internal side standing sheet 6 is fixed to the waist flap WF. Therefore, as shown in FIG. 27, a proximal edge E2 of the standing cuff WB for the wearer's waist is disposed on the waist flap F. The longitudinally inboard portion with respect to the proximal edge E2 defines a standing portion WZ, which is not fixed to the diaper body but free therefrom. It is preferable that the length L of the standing portion ZW in the longitudinal direction of the article is at least 10 mm. Particularly in the case of a diaper, the length L is preferably 30 mm to 80 mm.

The standing cuff WB is fixed so that the back end edge E3 of the standing sheet 6 is longitudinally inboard with respect to the back end E7 of the waist flap F by suitable distance, in this embodiment, 1 mm to 40 mm.

The internal side of the double standing sheet 6 is fixed, at its laterally end portion, to the wearer-side surface of the diaper. In this embodiment, as shown in FIG. 27, this internal side of the double standing sheet 6 is fixed, at its laterally outboard portion with respect to the proximal edge E4 of the standing cuff B, to the liquid pervious top sheet 1 with hot melt adhesive. In FIG. 27, a fixed portion HT formed between the standing sheet 6 and the liquid pervious top sheet 1 with hot melt adhesive is represented by dots. The external side of the double standing sheet 6 is fixed to the standing sheet 4 at its laterally outboard portion with hot melt adhesive. This fixed portion HB is disposed laterally outboard with respect to a line E5 and longitudinally outboard with respect to a line E6. Here, among the stretching members 5A and 5A for contacting within the standing cuff B, the line E5 is laterally outboard one, while among the stretching members 7A and 7A for contacting within the standing cuff WB, the line E6 is longitudinally outboard one. In FIG. 27, in the standing portion ZW of the standing cuff WB a portion fixed to the standing sheet 4 with hot melt adhesive is represented by HB.

Under such positional relation, the stretching members 7A, 7A for contacting extend in the vicinity of the distal edge E1 of the standing cuff WB, while the stretching members 7B, 7B, 7B for standing extend in the vicinity of the proximal edge E2 of the standing cuff WB. Accordingly, by means of the contracting force by the stretching members 7A, 7A and 7B, 7B, 7B, the standing cuff WB is able to stand. Further, by the stretching members 7B, 7B, 7B for standing, standing cuff WB is gathered so that the waist flap WF is not required to be gathered. In this case, lateral stretching does not occur in this diaper and it is easy to determine the center position of the diaper. This prevents misalignment of the diaper in applying the diaper to the wearer. As a result, the diaper is functioning properly.

Figure 26A:
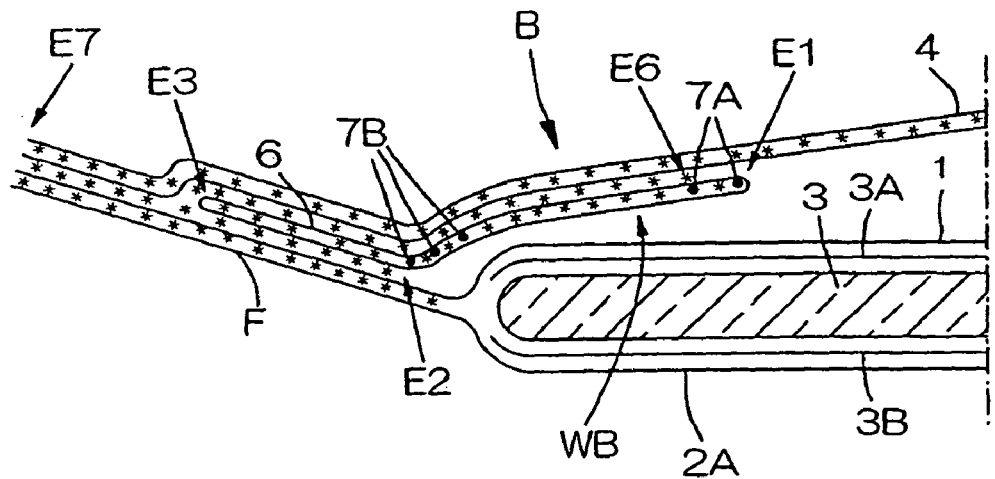
FIGS. 26A and 26B are sectional views taken on line XII-XII and line XI-XI of FIG. 25, respectively.
Figure 26B:
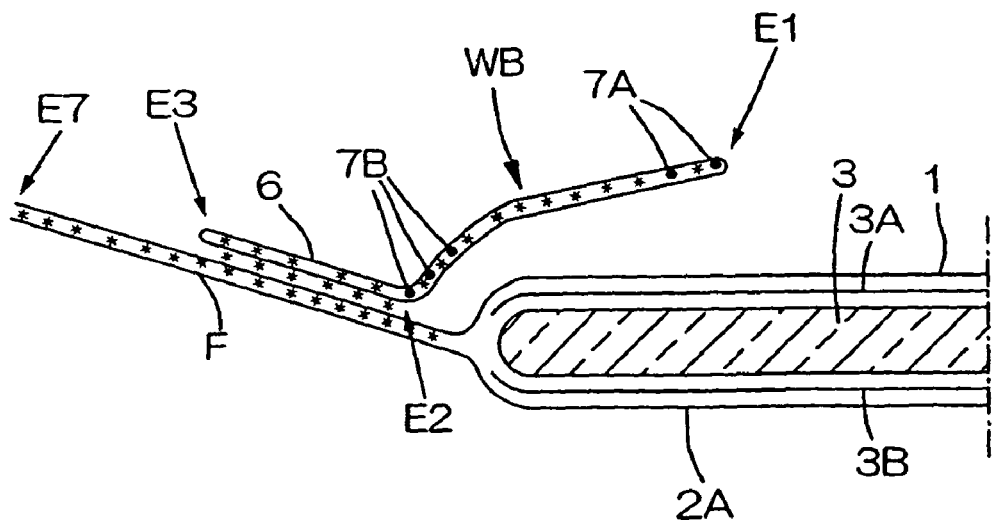

As shown in FIG. 26A, the standing cuff WB for the wearer's waist is pressed toward the diaper body by the standing cuff B in its laterally peripheral portion 26B (refer to FIG. 25). Accordingly, the standing cuff WB stands with a decreased height at the distal edge E1. On the other hand, as shown in FIG. 26B (refer to FIG. 25), there is no pressure by the standing cuff B in the laterally inboard portion thereof. Hence, the standing cuff WB will stand with the sufficient height by means of the stretching members 7B, 7B, and 7B for standing. However, the standing height of the distal edge E1 of the standing cuff WB is small in the portion 26B, which prevents the distal edge E1 of the standing cuff WB in the portion 26A from standing fully. As a result, in the laterally inboard portion of the standing cuff WB, it stands with an externally convex shape in its middle portion, as shown in FIG. 26B. By doing so, a pocket space if formed by the standing cuff WB, ensuring the enclosure of the complementary pad 100. At the same time, the waist flap WF is deformed and lifted and the absorbent core 3 is slightly deformed and lifted. Thus, the deeper pocket space can be obtained.

In addition, in such lifted state, the large contracting force by the stretching members 7B, 7B, 7B for standing is applied to the standing cuff WB itself. Therefore, the standing cuff WB is able to stand in the substantially vertical direction. At the same time, although the contracting force by the stretching member 7A, 7A for contacting is small, the standing cuff WB is able to surely stand also by means of this force. In spite of the small contracting force by the stretching member 7A, 7A for contacting, by means of the high contracting force by the stretching member 7B, 7B, 7B for standing, the standing ability of the standing cuff WB is surely attained. Further, because of the small contracting force by the stretching member 7A, 7A for contacting, too much pressure is not applied to the wearer's skin.

Figure 28:
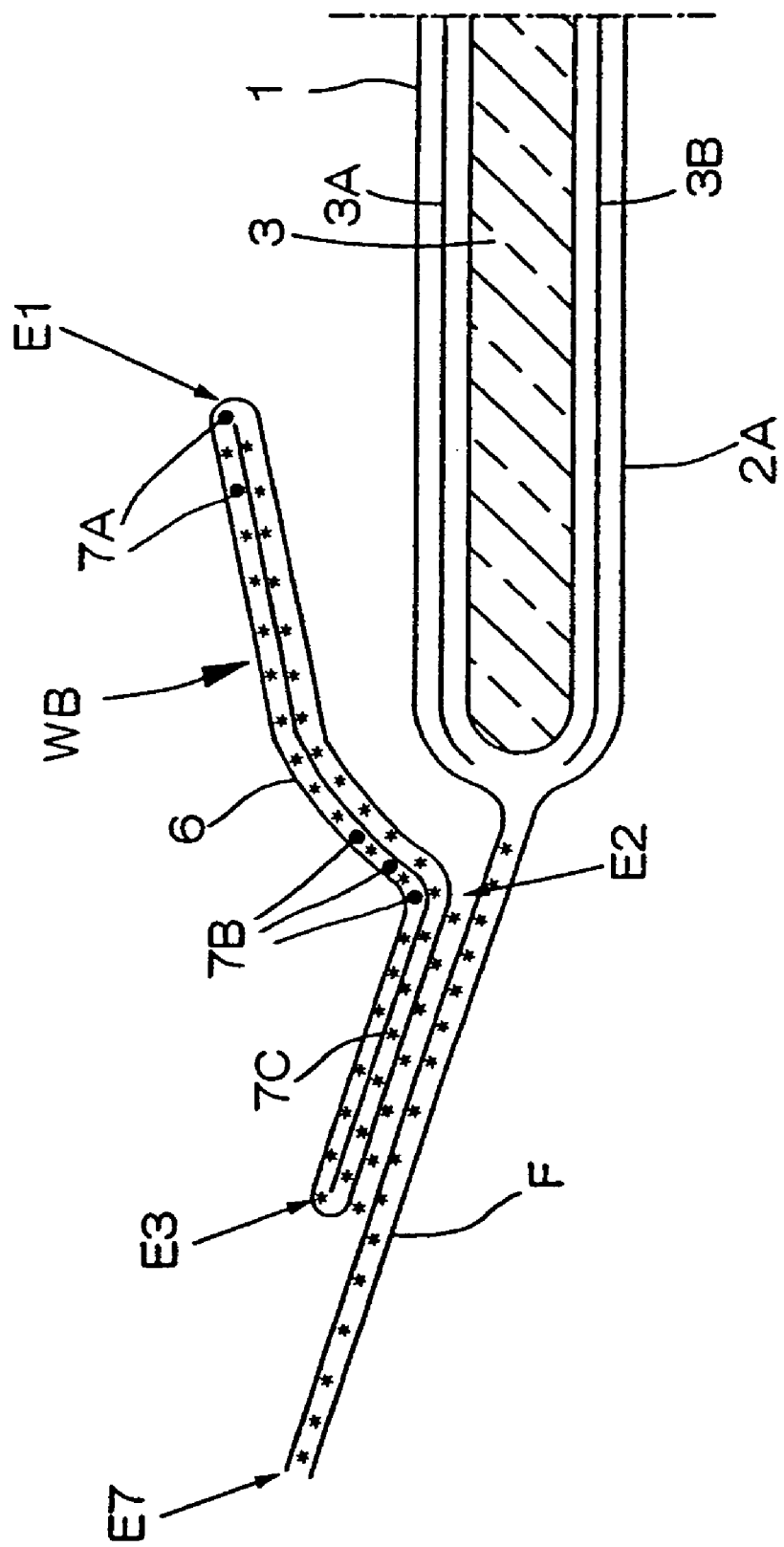
FIG. 28 is a laterally sectional view of a disposable diaper, which has a standing cuff for the wearer's waist.

As mentioned above, it is clear that the standing cuff WB is able to surely stand. Therefore, when the complementary pad 100 is provided so as to superpose on the wearer's side of the diaper, the standing cuff WB surely stands and encloses the complementary pad 100 without lying and bending back. As the material of the standing sheet 4 for the wearer's leg and the standing sheet 6 for the wearer's waist, a breathable and liquid impervious plastic film or non-woven fabric which is treated with silicone for water repellency may be used. Alternatively, as shown in FIG. 28 as an example of the standing cuff WB, for completely obviating the liquid perviousness, it is preferable to dispose water proof non-woven fabric or non-water proof non-woven fabric manufactured from plastic film or the like. As the non-woven fabric, polypropylene non-woven fabric manufactured with a melt blown method is more preferable. A sheet with the basis weight of 5 $g/m^2$ to 30 $g/m^2$ is folded and fixed to attain the double portion, and has the distal edge E1 spaced from the proximal edge E2. The stretching member is formed from strand of natural rubber, synthetic rubber, polyurethane or the like. The stretching members may be in the form of strands or a belt. In this embodiment, the standing cuff WB is able to stand in the substantially vertical direction through the means of application of the large contracting force by the stretching members 7B, 7B, and 7B. As the stretching members 7A, 7A for contacting, two strands of 560 denier urethane are provided for the lateral distance of 250 mm under the elongation of 200%. On the other hand, as the stretching members 7B, 7B, 7B for standing, three strands of 560 denier urethane are provided for the lateral distance of 250 mm under the elongation of 200% at the intervals of about 5 mm.

When the diaper with tape-tab fasteners is applied to the wearer, in the standing cuff WB, the elongation of the stretching member 7A for contacting is at most 60%, preferably 40% to 50%. In this embodiment, it is 50%. When under the elongation of 20% to 90% the stretching stress of the stretching member 7A for contacting is 0.05 N to 1 N and that of the stretching member 7B for standing is 0.10 N to 1.50 N, the wearer does not feel compressed. Further, a gap is not formed around the wearer's waist, resulting in high protection against the leakage It is clear from the foregoing description, in every embodiment, each standing cuff can stand surely with the sufficient height at the desirable position, thereby ensuring efficient protection against the leakage.

What is claimed is:

1. A disposable absorbent article comprising:
 a liquid pervious sheet;
 a liquid impervious sheet; and
 an absorbent structure including an absorbent core and being disposed between the liquid pervious sheet and the liquid impervious sheet, wherein
 standing cuffs for surrounding wearer's legs are provided at respective opposite sides of said disposable absorbent article,
 said liquid pervious sheet has a width greater than that of said absorbent structure so that said liquid pervious sheet has laterally extended portions extending beyond respective opposite sides of said absorbent structure,
 each of said standing cuffs comprises a standing sheet having two layers and stretching members provided under tension to the standing sheet between said two layers, wherein
  the standing sheet has a terminal proximal edge fixed directly to a corresponding one of the laterally extended portions of said liquid pervious sheet, said proximal edge defining a base line extending in a direction parallel to a longitudinal centerline of said disposable absorbent article,
  said two layered standing sheet comprising a standing portion, a folding back portion, and a surface contacting portion, the standing portion extending, on the corresponding one of the laterally extended portions, from the base line to the folding back portion in a lateral direction with respect to said base line toward the longitudinal centerline of said disposable absorbent article, the two layered sheet being folded back at the folding back portion, and the surface contacting portion extending, on the standing portion, from the folding back portion to a terminal distal edge in a lateral direction with respect to the longitudinal centerline toward the base line,
 two or more of said stretching members provided to the standing sheet are arranged adjacent the distal edge of said surface-contacting portion such that said two or more members are closer to the distal edge than the folding back portion, said two or more stretching members being spaced apart from each other, the distal edge being an edge which is distal from the folding back portion,
 at least one of said stretching members provided to the standing sheet is arranged in said standing portion at said base line such that said at least one stretching member is closer to the base line than the folding back portion,
 at least one of said stretching members provided to the standing sheet is arranged adjacent the folding back portion such that it is closer to the folding back portion than to the distal edge and the base line,
 during use of said disposable absorbent article, each of said standing cuffs is deformed by contractile force of said stretching members such that the standing portion extends in a substantially vertical direction relative to the corresponding one of the laterally extended portions and the base line and the surface-contacting portion pivots upwardly toward a corresponding one of the wearer's legs from the folding back portion but said distal edge remains laterally outwardly of the folding back portion,
 portions of the standing portion located at respective front and back ends of the disposable absorbent article are directly fixed to the pervious sheet, and portions of the surface-contacting portion located at the respective front and back ends of the disposable absorbent article are directly fixed to the respective portions of the standing portion so that said standing and surface contacting portions overlie each other and are parallel to each other and the liquid pervious sheet, the front and back ends respectively extending in a direction substantially perpendicular to a longitudinal direction of the disposable absorbent article, and
 the respective opposite sides of the disposable absorbent article extending further outward from the respective laterally extended portions.

2. The disposable absorbent article as defined in claim 1, wherein the folding back portion is located outside of an area over said absorbent core.

3. The disposable absorbent article as defined in claim 1, wherein
 a back sheet is disposed on a back-side of said liquid impervious sheet, and
 said liquid impervious sheet has a width greater than that of said absorbent structure so that said liquid impervious sheet has laterally extended portions extending beyond said respective opposite sides of said absorbent structure.

4. The disposable absorbent article as defined in claim 1, wherein the two or more of said stretching members arranged in the vicinity of said distal edge of said surface-contacting portion has a size of 400 d to 640 d and a contraction percentage of 160% to 300%, and the at least one of said stretching members arranged in said standing portion has a size of 640 d to 2100 d and a contraction percentage of 150% to 250%.

5. The disposable absorbent article as defined in claim 1, further comprising stretching members disposed between said liquid impervious sheet and said absorbent structure to lift the respective opposite sides of said absorbent structure, the stretching members extending along a direction parallel to the longitudinal centerline of said disposable absorbent article.

6. The disposable absorbent article as defined in claim 5, wherein said absorbent core has a hourglass-like shape having a widest width portion and a narrowest width portion, the narrowest width portion including side portions for respectively encircling the wearer's legs, and said stretching members disposed between said liquid impervious sheet and said absorbent structure are arranged to overlap the widest width portion, but not overlap the narrowest width portion.

7. The disposable absorbent article as defined in claim 1, further comprising stretching members disposed between said liquid impervious sheet and said absorbent core to lift the respective opposite sides of said absorbent structure, the stretching members extending along a direction parallel to the longitudinal centerline of said disposable absorbent article.

* * * * *